US008536205B2

(12) United States Patent
Branda et al.

(10) Patent No.: US 8,536,205 B2
(45) Date of Patent: Sep. 17, 2013

(54) PHOTOCHROMIC AND ELECTROCHROMIC COMPOUNDS AND SYNTHESIS AND USE THEREOF

(75) Inventors: Neil R. Branda, North Vancouver (CA); Bettina Wuestenberg, Ritterhude (DE); Vincent Lemieux, Mont-tremblant (CA); Michael Adams, Vancouver (CA); Simon Gauthier, Ottawa (CA)

(73) Assignee: Switch Materials Inc., Vancouver, British Columbia (CA)

( * ) Notice: Subject to any disclaimer, the term of this patent is extended or adjusted under 35 U.S.C. 154(b) by 969 days.

(21) Appl. No.: 11/915,530

(22) PCT Filed: May 25, 2006

(86) PCT No.: PCT/CA2006/000862
§ 371 (c)(1),
(2), (4) Date: Mar. 10, 2010

(87) PCT Pub. No.: WO2006/125317
PCT Pub. Date: Nov. 30, 2006

(65) Prior Publication Data
US 2010/0190868 A1 Jul. 29, 2010

Related U.S. Application Data

(60) Provisional application No. 60/684,715, filed on May 25, 2005.

(51) Int. Cl.
*A61K 31/4427* (2006.01)
*C07D 401/06* (2006.01)
(52) U.S. Cl.
USPC ........................................ 514/343; 546/276.4
(58) Field of Classification Search
USPC ............... 514/422, 343; 548/517; 546/276.4
See application file for complete search history.

(56) References Cited

U.S. PATENT DOCUMENTS

| | | | |
|---|---|---|---|
| 5,342,909 A | 8/1994 | Grubbs et al. | |
| 5,604,002 A | 2/1997 | Tsujioka et al. | |
| 5,736,065 A | 4/1998 | Nakaso et al. | |
| 5,776,954 A * | 7/1998 | de Laszlo et al. | 514/340 |
| 5,849,851 A | 12/1998 | Grubbs et al. | |
| 6,123,952 A | 9/2000 | Lagrange | |
| 6,359,150 B1 | 3/2002 | Fukudome et al. | |
| 6,479,604 B1 | 11/2002 | Kim et al. | |
| 6,787,621 B2 | 9/2004 | Kim et al. | |
| 6,846,934 B2 | 1/2005 | Kim et al. | |
| 6,884,553 B2 | 4/2005 | Irie et al. | |
| 7,041,763 B2 | 5/2006 | Branda et al. | |
| 7,057,054 B2 | 6/2006 | Irie | |
| 7,101,497 B2 | 9/2006 | Tanaka et al. | |
| 7,135,132 B2 | 11/2006 | Kim et al. | |
| 7,154,657 B2 | 12/2006 | Poll et al. | |
| 2002/0142248 A1 | 10/2002 | Dubois et al. | |
| 2003/0086978 A1 | 5/2003 | Kim et al. | |
| 2003/0118924 A1 | 6/2003 | Kim et al. | |
| 2006/0053975 A1 | 3/2006 | Shibahashi et al. | |
| 2006/0073392 A1 | 4/2006 | Erben et al. | |
| 2006/0079653 A1 | 4/2006 | Dunaev et al. | |
| 2006/0091364 A1 | 5/2006 | Alfimov et al. | |
| 2006/0097225 A1 | 5/2006 | Yamamoto et al. | |
| 2006/0240197 A1 | 10/2006 | Branda et al. | |
| 2007/0003847 A1 | 1/2007 | Chopra et al. | |

FOREIGN PATENT DOCUMENTS

| | | |
|---|---|---|
| CN | 1152110 C | 6/2004 |
| EP | 0446717 A2 | 9/1991 |
| EP | 0698605 A1 | 2/1996 |
| FR | 2774998 A1 | 8/1999 |
| JP | 1022872 A | 1/1989 |
| JP | 3264573 A | 11/1991 |
| JP | 5112637 A | 5/1993 |
| JP | 6240242 | 8/1994 |
| JP | 8119963 | 5/1996 |
| JP | 10152679 | 6/1998 |
| JP | 11256147 | 9/1999 |
| JP | 2002265465 | 9/2002 |
| WO | 9101312 A1 | 2/1991 |
| WO | 9931107 A1 | 6/1999 |
| WO | 0206361 A2 | 1/2002 |
| WO | 2004015024 A1 | 2/2004 |
| WO | 2006037279 A1 | 4/2006 |

OTHER PUBLICATIONS

Deng, X et al; Communications to the Editor; Journal of the American Chemical Society, vol. 123, 2001; pp. 7703-7704, XP002566023.
Krayushkin M. M et al.; Synthesis and Structure of 5-Indolyl-6-thienyl-1,2,4-triazines; Russian Journal of Organic Chemistry, Nauka/Interperiodica, MO; vol. 41, No. 6; Jun. 1, 2005; pp. 875-883, XP019302034 ISSN:1608-3393.
Wigglesworth T.J., et al.; Advanced Materials, vol. 16, No. 2, 2004; pp. 123-125, XP002566024.
Huang Z.N. et al.; Facile Synthesis of Novel Photochromic 1,2-Diheteroaryl-Substituted Cycloalkenes by Titanium-Induced Intramolecular Coupling Reaction; vol. 8, 1998; pp. 1092-1094, XP002566025.
Shrestha, S.M., et al.; Synthesis of Novel Thermally Irreversible Photochromic 1-Aryl-1,3-butadiene Derivatives; Bull. Chem. Society JPN.; vol. 76, 2003; pp. 363-367, XP002566026.
Supplementary European Search Report for European Patent Application No. 06 74 1571.1; Jan. 29, 2010.

(Continued)

*Primary Examiner* — Taofiq A Solola
(74) *Attorney, Agent, or Firm* — Merchant & Gould P.C.

(57) ABSTRACT

Photochromic and electrochromic hexadiene compounds that are reversibly convertible between ring-open and ring-closed isomeric forms. The conversion between the different isomeric forms may be induced by light or electricity. The compounds may include a charge transfer moiety including electron donor and acceptor groups. The electron donor and acceptor are linearly conjugated in the ring-open form to enable electron transfer but are electrically insulated in the ring-closed form. Photoresponsive compounds may be synthesized by any of several methods disclosed, e.g., by reacting diene precursors with dienophiles in a condensation reaction. The compounds may be utilized in reactivity-gated photochromic or electrochromic applications. Compounds may be used in a method to selectively release a releasable agent, such as a small molecule.

36 Claims, 6 Drawing Sheets

(56) References Cited

OTHER PUBLICATIONS

Irie et al.; Photochromism of diarylethenes having thiophene oligomers as the aryl groups; Tetrahedron; 1997; pp. 12263-12271; vol. 53, No. 36.

Irie et al.; Photochromic diarylethenes with intralocking arms; J. Am. Chem. Soc.; 1994; pp. 9894-9900; vol. 116.

Irie et al.; Thermally irreversible photochromic systems. Reversible photocyclization of diarylethene derivatives; J. Org. Chem.; 1988; pp. 803-808; vol. 53.

Ivanov et al.; Synthesis of substituted 1,2,4-triazines based on 1,2-bis(2,5-dimethyl-3-thienyl)ethanedione; Chemistry of Heterocyclic Compounds; 2001; pp. 85-90; vol. 37, No. 1.

Kawai et al.; A dual-mode molecular switching device: Bisphenolic diarylethenes with integrated photochromic and electrochromic properties; Chem. Eur. J.; 1995; pp. 285-293; vol. 1, No. 5.

Kawai et al.; Novel photochromic conducting polymer having diarylethene derivative in the main chain; Chemistry Letters; 1999; pp. 905-906.

Kim et al.; Photoinduced refractive index change of a photochromic diarylethene polymer; Macromolecules; 1999; pp. 4855-4860; vol. 32.

Koshido et al.; Optical and electrochemical properties of cis-1,2-dicyano-1,2-bis(2,4,5-trimethyl-3-thienyl)ethene; J. Phys. Chem.; 1995; pp. 6110-6114; vol. 99.

Kumar; Photochemistry of azobenzine-containing polymers; Chem. Rev.; 1989; pp. 1915-1925; vol. 89.

Lucas et al.; A new class of photochromic 1,2-diarylethenes; synthesis and switching properties of bis(3-thienyl) cyclopentenes; Chem. Commun.; 1998; pp. 2313-2314.

Lucas et al.; A new synthetic route to symmetrical photochromic diarylperfluorocyclopentenes; Tetrahedron Letters; 1999; pp. 1775-1778; vol. 40.

Lyubimov et al.; Photochromic network polymers; Journal of Photochemistry and Photobiology A: Chemistry; 1999; pp. 55-62; vol. 120.

Miki et al.; Photo- and electro-chromism of a 1,4-anthraquinone derivative. A multi-mode responsive molecule; Chem. Commun.; 1997; pp. 925-926.

Montalban et al.; Synthesis and ring opening metathetic polymerisation of porphyrazine benzonorbornadiene derivatives; Tetrahedron Letters; 1999; pp. 8151-8155; vol. 40.

Moriyama et al.; Electrochemical cyclization/cycloreversion reactions of diarylethenes; Org. Lett.; 2005; pp. 3315-3318; vol. 7, No. 15.

Mulder et al.; Photocontrolled release and uptake of a porphyrin guest by dithienylethene-tethered βcyclodextrin host dimers; Chem. Eur. J.; 2004; pp. 1114-1123; vol. 10.

Munakata et al.; Reversible photochromism of a crystalline dithienylethene copper(I) polymer; J. Am. Chem. Soc.; 1996; pp. 3305-3306; vol. 118.

Myles et al.; Novel synthesis of photochromic polymers via ROMP; Org. Lett.; 2000; pp. 2749-2751; vol. 2, No. 18.

Myles et al.; Novel photochromic homopolymers based on 1,2-bis(3-thienyl)cyclopentenes; Macromolecules; 2003; pp. 298-303; vol. 36.

Nakashima et al.; Synthesis of polystyrene and poly(alkyl methacrylate)s having photochromic dithienylethene pendant groups; Polymer Journal; 1998; pp. 985-989; vol. 30, No. 12.

Nakashima et al.; Synthesis of silsesquioxanes having photochromic dithienylethene pendant groups; Macromol. Chem. Phys.; 1999; pp. 683-692; vol. 200.

Nakayama et al.; Thermally irreversible photochromic systems. Photoreaction of diarylethene derivatives with imidazo[1,2-a]pyridine rings; Bull. Chem. Soc. Jpn.; 1991; pp. 202-207; vol. 64, No. 1.

Newell et al.; 2-(2-arylvinyl)-9,10-anthraquinones: Combined electro- and photo-chromic properties for molecular switching; J. Chem. Soc., Chem. Commun.; 1992; pp. 800-801.

Norsten et al.; Photoregulaton of fluorescence in a porphyrinic dithienylethene photochrome; J. Am. Chem. Soc.; 2001; pp. 1784-1785; vol. 123.

Otto et al.; Syntheses and UV/Vis properties of amino-functionalized fulgimides; Eur. J. Org. Chem.; 2003; pp. 2409-2417.

Peters et al.; Electrochemically induced ring-closing of photochromic 1,2-dithienylcyclopentenes; Chem. Comm. 2003; pp. 954-955.

Peters et al.; Novel photochromic compounds based on the 1-thienyl-2-vinylcyclopentene backbone; Org. Lett.; 2003; pp. 1183-1186; vol. 5, No. 8.

Peters et al.; Electrochromism in photochromic dithienylcyclopentenes; J. Am. Chem. Soc.; 2003; pp. 3404-3405; vol. 125, No. 12.

Robson et al.; A new and highly efficient Grubbs initiator for ring-opening metathesis polymerization; Macromolecules; 1999; pp. 6371-6373; vol. 32.

Saika et al.; Multi-mode chemical transducers. Part 2. Electrochromic and photochromic properties of azoquinone compounds; J. Chem. Soc. Perkin Trans.; 1993; pp. 1181-1186; Vol. 2.

Salakhov et al.; Synthesis of the n-arylimides of endo- and exo-bicyclo[2.2.1]-hept-5-ene-2,3-dicarboxylic acid and their adducts with hexachlorocyclopentadiene; J. Org. Chem.; USSR English Translation; 1979; pp. 2106-2112.

Sanford et al.; Mechanism and activity of ruthenium olefin metathesis catalysts; J. Am. Chem. Soc.; 2001; pp. 6543-6554; vol. 123.

Stellacci et al.; A high quantum yield diarylethene-backbone photochromic polymer; Advanced Materials; 1999; pp. 292-295; vol. 64.

Takeshita et al.; Novel saccharide tweezers with a diarylethene photoswitch; Chem. Commun.; 1996; pp. 1807-1808.

Takeshita et al.; Alkali metal ion effect on the photochromism of 1,2-bis(2,4-dimethylthien-3-yl)-perfluorocyclopentene having benzo-15-crown-5 moieties; Tetrahedron Letters; 1998; pp. 7717-7720; vol. 39.

Tsujioka et al.; Organic bistable molecular memory using photochromic diarylethene; Appl. Phys. Lett.; Aug. 4, 2003; pp. 937-939; vol. 83, No. 5.

Uchida et al.; Photochromism of diarylethenes on porous aluminum oxide: Fatigue resistance and redox potentials of the photochromes; Chemistry Letters; 2001; pp. 366-367.

Verbiest et al.; Second-order nonlinear optical materials: Recent advances in chromophore design; J. Mater. Chem.; 1997; pp. 2175-2189; vol. 7, No. 11.

Warshawsky et al.; Photochromic polysulfones. 1. Synthesis of polymeric polysulfone carrying pendant spiropyran and spirooxazine groups; Ind. Eng. Chem. Res.; 1995; pp. 2825-2832; vol. 34.

Willner et al.; Photoswitchable binding of substrates to proteins: Photoregulated binding of a-d-mannopyranose to concanavalin a modified by a thiophenefulgide dye; J. Am. Chem. Soc.; 1992; pp. 3150-3151; vol. 114.

Wu et al.; Living ring-opening metathesis polymerization of bicyclo[3.2.0]heptene catalyzed by a ruthenium alkylidene complex; Macromolecules; 1993; pp. 4975-4977; vol. 26.

Yu et al.; Synthesis and solvent effect on absorption spectra of pyrryl substituted fulgides; Youji Huaxue; 1993; pp. 590-596; vol. 13, No. 6.

Zhi et al. A multi-functional electro-optical molecular device. The photoelectrochemical behavior of spirobenzopyrans in dimethylformamide; Ber. Bunsenges. Phys. Chem.; 1995; pp. 32-39; vol. 99, No. 1.

Zhi et al.; Photoelectrochromic properties of a spirobenzopyran derivative; Journal of Photochemistry and Photobiology A: Chemistry; 1995; pp. 91-97; vol. 92.

Zhou et al.; Photoelectrochromic dithienylperfluorocyclopentene derivatives; Chemistry Letters; 2004; pp. 1006-1007; vol. 33, No. 8.

Search Report for International Patent Application No. PCT/CA2006/000862; Sep. 12, 2006.

Canadian Patent Office Examiner's Report for related Application No. CA 2,609,887; dated Jul. 5, 2012.

Extended European Search Report for EP Patent Application No. 06741571.1 mailed Feb. 10, 2010, 12 pgs.

Office Communication for EP Patent Application No. 06741571.1 mailed Apr. 30, 2010, 1 pg.

Office Communication for EP Patent Application No. 06741571.1 mailed Jun. 30, 2011, 4 pgs.

Dinescu et al., "Synthesis and photochromic properties of helically locked 1,2-dithienylethenes", *ChemComm,* vol. 24, pp. 2497-2498, The Royal Society of Chemistry 1999.

Asiri; Synthesis and photochromic properties of E,E-Bis-a-(2,5-dimethyl-3-furyl)ethylidenesuccinic anhydride and its 2-dicyanomethylene derivative; Kuwait J. Sci. Eng.; 1999; pp. 283-288; vol. 26, No. 2.

Badland et al.; Photochromic heteroaromatic thiofulgides and dimethoxybutanoic acid lactones; Chem. Commun.; 2000; pp. 1567-1568.

Bechinger et al.; Photoelectrochromic windows and displays; Nature; Oct. 17, 1996; pp. 608-610; vol. 383.

Belen'Kii et al.; Synthesis of 4-hetaryl-5,6-(2,5-dimethyl-3-thienyl)-2-phenyl-4h-thiazines and investigation of their photochromism; Chemistry of Heterocyclic Compounds; 2005; pp. 86-92; vol. 41, No. 1.

Bolm et al.; Synthesis of catalytically active polymers by means of ROMP: An effective approach toward polymeric homogeneously soluable catalysts; J. Org. Chem.; 1999; pp. 5730-5731; vol. 64.

Browne et al.; Oxidative electrochemical switching in dithienylcyclopentenes, Part 1: Effect of electronic perturbation of the efficiency and direction of molecular switching; Chem. Eur. J.; 2005; pp. 6414-6429; vol. 11.

Browne et al.; Oxidative electrochemical switching in dithienylcyclopentenes, Part 2: Effect of substitution and asymmetry on the efficiency and direction of molecular switching and redox stability; Chem. Eur. J.; 2005; pp. 6430-6441; vol. 11.

Buchholtz et al.; Synthesis of new photochromic polymers based on phenoxynaphthacenequinone; Macromolecules; 1993; pp. 906-910; vol. 26.

Calcagno et al.; Understanding the structural properties of a homologous series of bis-diphenylphosphine oxides; Chem. Eur. J.; 2000; pp. 2338-2349; vol. 6, No. 13.

Darcy et al.; Photochromic heterocyclic fulgides. Part 2. Electrocyclic reactions of (E)-a-2,5-dimethyl-3-furylethylidene(alkyl-substituted methylene)-succinic anhydrides; J.C.S. Perkin I; 1981; pp. 202-205.

De Jong et al.; Photochromic properties of perhydro- and perfluorodithienylcyclopentene molecular switches; Eur. J. Org. Chem.; 2003; pp. 1887-1893.

Di Bella; Second-order nonlinear optical properties of transition metal complexes; Chem. Soc. Rev.; 2001; pp. 355-366; vol. 30.

Fraysse et al.; Synthesis and properties of dinuclear complexes with a photochromic bridge: An intervalence electron transfer switching "on" and "off"; Eur. J. Inorg. Chem.; 2000; pp. 1581-1590.

Gilat et al.; Light-triggered electrical and optical switching devices; J. Chem. Soc., Chem. Comm.; 1993; pp. 1439-1442.

Gilat et al.; Light-triggered molecular devices: Photochemical switching of optical and electrochemical properties in molecular wire type diarylethene species; Chem. Eur. J.; 1995; pp. 275-284; vol. 1, No. 5.

Gorodetsky et al.; Reductive electrochemical cyclizaton of a photochromic 1,2-dithienylcyclopentene dication; Angew. Chem. Int. Ed.; 2004; pp. 2812-2815; vol. 43.

Grubbs et al.; Polymer synthesis and organotransition metal chemistry; Science; Feb. 17, 1989; pp. 907-915; vol. 243, No. 4893.

Guirado et al.; Understanding electrochromic processes initiated by dithienylcyclopentene cation-radicals; J. Phys. Chem. B; 2005; pp. 17445-17459; vol. 109, No. 37.

Heller et al.; A new class of photochromic compounds exemplilfied by e-5-dicyanomethylene-4-(dialkyl and dicycloalkyl)methylene[1-(2,5-methyl-3-furyl) and (2-methyl-5-phenyl-3-thienyl)ethylidene]tetrahydrofuran-2-ones; J. Chem. Soc., Chem. Commun.; 1994; pp. 2713-2714.

Heller et al.; Fulgides and fulgimides for practical applications; Mol. Cryst. Liq. Cryst.; 1994; pp. 79-86; vol. 246.

Heller et al.; The design and development of new thermally stable infra-red active photochromic compounds; Mol. Cryst. Liq. Cryst.; 1997; pp. 73-80; vol. 297.

Ichimura; Photochromic polymers; Organic Photochromic and Thermochromic Compounds, vol. 2; 1999; pp. 9-63.

Iyoda et al.; A multi-mode chemical transducer 1 new conjugated function of photochromism and electrochromism of azo-quinone compound; Tetrahedron Letters; 1989; pp. 5429-5432; vol. 30, No. 40.

Ireland et al.; Tetra-substituted ethylenes; Synthetic Communications; 1976; pp. 185-191; vol. 6, No. 3.

Irie; Photochromic dithienylethenes for molecular photonics; Phosphorus, Sulfur, and Silicon; 1997; pp. 95-106; vols. 120-121.

Irie; Diarylethenes for memories and switches; Chem. Rev.; 2000; pp. 1685-1716; vol. 100.

Irie; Photoswitchable molecular systems based on diarylethenes; Molecular Switches; 2001; pp. 37-62.

Irie; Diarylethenes with heterocyclic aryl groups; Organic Photochromic and Thermochromic Compounds, vol. 1; 1999; pp. 207-222.

* cited by examiner ent
PHOTOCHROMIC AND ELECTROCHROMIC COMPOUNDS AND SYNTHESIS AND USE THEREOF

RELATED APPLICATIONS

This patent application is a U.S. National Phase of International Patent Application No. PCT/CA2006/000862, filed May 25, 2006, which claims priority to U.S. Patent Application No. 60/684,715, filed May 25, 2005, the disclosures of which are incorporated herein by reference in their entirety.

TECHNICAL FIELD

This application relates to novel photochromic and electrochromic compounds, methods of making the compounds, and uses thereof.

BACKGROUND

Photochromism is defined as the reversible photoinduced transformation of a chemical species between two isomers having different absorption spectra [1]. The photochemical reaction is accompanied by a difference in properties other than the absorption of light such as the emission of light, refractive index, polarization, redox potentials, dipole moments, host-guest interactions and chemical reactivity. The changes in these properties implies that photoresponsive compounds can contribute to the advancement of numerous, diverse applications, where it is desirable that a given property is regulated. Applications include, but are not limited to, photonic devices such as (1) actinometers, (2) sensors and dosiometers, (3) novelty items such as inks, paints and other dyes, (4) variable transmission filters, (5) optical information storage systems, (6) molecular switches that can be incorporated into molecule-based wires, circuitry and machinery, (7) opto-electronic systems, (8) reversible holographic systems, (9) electro-optical devices such as waveguides, (10) the light-induced delivery of biologically, medically and synthetically relevant compounds, and (11) photoregulation of polymers.

[1] Organic Photochromic and Thermochromic Compounds; Crano, J. C., Guglielmetti, R. J., Eds.; Plenum Press: New York, 1999; Vols. 1 and 2. M. Irie, in *Molecular Switches*, (Ed.: B. L. Feringa), Wiley-VCH, Weinheim, Germany, 2001, pp. 37-62; Special issue on photochromism: M. Irie, *Chem. Rev.* 2000, 100, 1685-1716.

Electrochromic molecules which change color when electrochemically oxidized or reduced are also well known in the prior art [2]. For example, compounds exhibiting electrochomism, including "dual mode" compounds having both electrochromic and photochromic properties, are described in applicant's PCT application No. PCT/CA2003/001216 (WO 2004/015024) which is hereby incorporated by reference.

[2] *Electrochromism: Fundamentals and Applications*, Monk, P. M. S.; Mortimer, R. J.; Rosseinky, D. R., Eds., VHC: New York, 1995.

Numerous optical technologies such as waveguiding, data storage, variable reflectance in eyewear and filters, and sensors rely on the non-linear optical (NLO) properties of materials [3]. There has been a recent and enormous growth in the interest in NLO materials and some estimates claim that over one third of the existing electronic technologies currently used for data transmission and processing will be replaced by the faster electro-optic and photonic analogues. The success of these devices requires the development of new functional NLO materials with large and rapid NLO responses. NLO properties originate from molecules that have strong charge transfer excitations within non-centrosymmetric structures due to a polarisable π-conjugated framework, where electron donor ('D') and acceptor ('A') groups at the ends of the linear π-pathway creates an asymmetric charge distribution.

[3] Di Bella, S. *Chem. Soc. Rev.* 2001, 30, 355. Verbiest, T.; Houbrechts, S.; Kauranen, M.; Clays, K.; Persoons, A. *J. Mater. Chem.* 1997, 7, 2175.

In systems that undergo "gated" photochromism, irradiation with light does not trigger a molecular transformation unless another external stimulus such as electricity, other photons, heat, or a chemical is applied before or during the irradiation period. By combining more than one input stimulus in molecular switching technologies, "logic-based" devices can be developed. In reactivity-gated photochromism or electrochromism, an initial chemical reaction must occur to convert the compound from a non-photo- or electroactive state to a photo- or electroactive state. Such systems may be particularly useful for sensing and dosiometry applications.

Molecular architectures that incorporate the 1,3,5-hexatriene motif are often photoresponsive and undergo reversible ring-closing and ring-opening reactions. Hexatriene compounds such as diarylethenes make up an important class of photoswitchable compounds [4] and many of the derivatives are also electroactive [5]. These particular compounds typically undergo thermally irreversible photoreactions with a high degree of fatigue resistance. They are the focus of numerous current research efforts. Previous reports of reactivity-gated photochromism using diarylethenes describe systems that operate based on the fact that the presence of the gate input affects the quantum yield of the ring-closing and ring-opening reactions by biasing the conformational equilibrium of the systems [6]. In many cases the effects are small.

[4] M. Irie, in *Molecular Switches*, (Ed. B. L. Feringa), Wiley-VCH, Weinheim 2001, 37-60.
[5] Peters, A.; Branda, N. R. *Chem. Commun.* 2003, 954. Gorodetsky, B.; Samachetty, H.; Donkers, R. L.; Workentin, M. S.; Branda, N. R. *Angew. Chem. Int. Ed.* 2004, 43, 2812. Koshido, T.; Kawai, T.; Yoshino, K. *J. Phys. Chem.* 1995, 99, 6110. Peters, A. Branda, N. R. *J. Am. Chem. Soc.* 2003, 125, 3404. Zhou, X.-H.; Zhang, F.-S.; Yuan, P.; Sun, F.; Pu, S.-Z.; Zhao, F.-Q.; Tung, C.-H. *Chem. Lett.* 2004, 33, 1006. Moriyama, Y.; Matsuda, K.; Tanifuji, N.; Irie, S.; Irie, M. *Org. Lett.* 2005, 7, 3315. Brown, W. R.; de Jong, J. J. D.; Kudernac, T.; Walko, M.; Lucas, L. N.; Uchida, K.; van Esch, J. H.; Fering a, B. L. *Chem. Eur. J.* 2005, 11, 6414. Brown, W. R.; de Jong, J. J. D.; Kudernac, T.; Walko, M.; Lucas, L. N.; Uchida, K.; van Esch, J. H.; Feringa, B. L. *Chem. Eur.* 12005, 11, 6430. Guirado, G.; Coudret, C.; Hliwa, M.; Launay, J.-P. *J. Phys. Chem. B.* 2005, 109, 17445. Tsujioka, T.; Kondo, H. *App. Phys. Lett.* 2004, 83. 937.
[6] Takeshita, M.; Irie, M. *J. Chem. Soc., Chem. Comm.* 1996, 1807. Takeshita, M.; Soong, C. F.; Irie, M. *Tetrahedron Lett.* 1998, 39, 7717. Irie, M.; Miyatake, O.; Uchida, K.; Eriguchi, T. J. *Am. Chem. Soc.* 1994, 116, 9894.

The development of novel variations of the versatile 1,3,5-hexatriene architecture and convenient methods to prepare them is an important goal. The incorporation of a donor-it-acceptor motif (D-π-A) which can be reversibly created and broken in a controlled manner as part of the photochromic reaction of the novel architecture would be advantageous for the development of new functional NLO materials. It would also be beneficial to develop new compounds suitable for reactivity-gated photochromism or electrochromism, including gated systems enabling controlled release of small molecules and the like.

SUMMARY OF INVENTION

This application relates to the structure, synthesis, characterization and use of a series of novel hexatriene compounds. In one embodiment, each compound of the invention is reversibly convertible between a first ring-open isomeric form represented by the formula I(o) and a second ring-closed isomeric form represented by I(c)

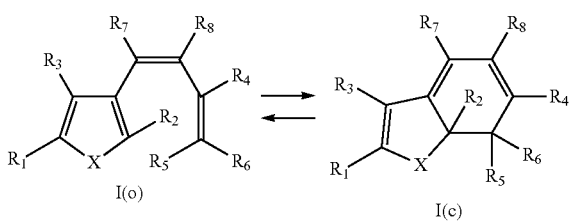

wherein X is a heteroatom selected from the group consisting of S, N and O; $R_1$ is selected from the group consisting of H, a halogen, alkyl, aryl and substituted aryl; $R_2$ is selected from the group consisting of alkyl, aryl and substituted aryl; $R_3$ is selected from the group consisting of H and alkyl; $R_4$ is selected from the group consisting of H, alkyl, aryl, substituted aryl, an electron-donating group, an electron-accepting group, and a constituent of an optionally substituted heterocycle; $R_5$ is selected from the group consisting of alkyl, aryl, substituted aryl, an electron-donating group and an electron-accepting group; $R_6$ is selected from the group consisting of alkyl, aryl, substituted aryl, an electron-donating group, an electron-accepting group and a constituent of an optionally substituted heterocycle; and $R_7$ and $R_8$ are each selected from the group consisting of a constituent of a 5 membered ring comprising H or a halogen or an optionally substituted 6 membered ring. In an embodiment when $R_4$ and $R_6$ are constituents of a thiophene ring and $R_5$ is an alkyl, aryl or substituted aryl, then $R_7$ and $R_8$ are constituents of an optionally substituted 6 membered ring. In another embodiment when $R_7$ and $R_8$ are constituents of a 5 membered halogenated ring, then $R_4$, $R_5$ and $R_6$ are independently not an alkyl or aryl.

The hexatriene compound represented by formula I(o) is reversibly convertible between the first and second forms in response to a light and/or electrical stimulus. For example, compound I may be converted from the first form to the second form by the application of ultraviolet light and from the second form to the first form by visible light.

In one embodiment of the invention, the compound may include both a charge transfer moiety comprising an electron donor and an electron acceptor and a switching moiety reversibly convertible between a first ring-open form and a second ring-closed form in response to a light or electrical stimulus. In this embodiment the electron donor and electron acceptor are linearly conjugated when the switching moiety is in the first form and electronically insulated when the switching moiety is in the second form. Accordingly, the charge transfer and isomeric switching functionalities of the compound are effectively integrated.

In one embodiment of the invention, compounds of the invention may be used in a method to selectively release a releasable agent, such as a small molecule. According to this method, a photochemically inert precursor compound is reacted with the releasable agent to form a carrier compound comprising a switching moiety, the switching moiety being reversibly convertible between a thermally unstable form and a thermally stable form. The switching moiety may be selectively converted between the first and second forms to cause controlled release of the releasable agent from the carrier compound. The gated reaction between the precursor and the releasable agent may be, for example, a reversible condensation reaction.

Methods for synthesizing the hexatriene compounds of the invention and precursors thereof are also described.

BRIEF DESCRIPTION OF DRAWINGS

In drawings which are intended to illustrate embodiments of the invention.

DESCRIPTION

Figure 1:
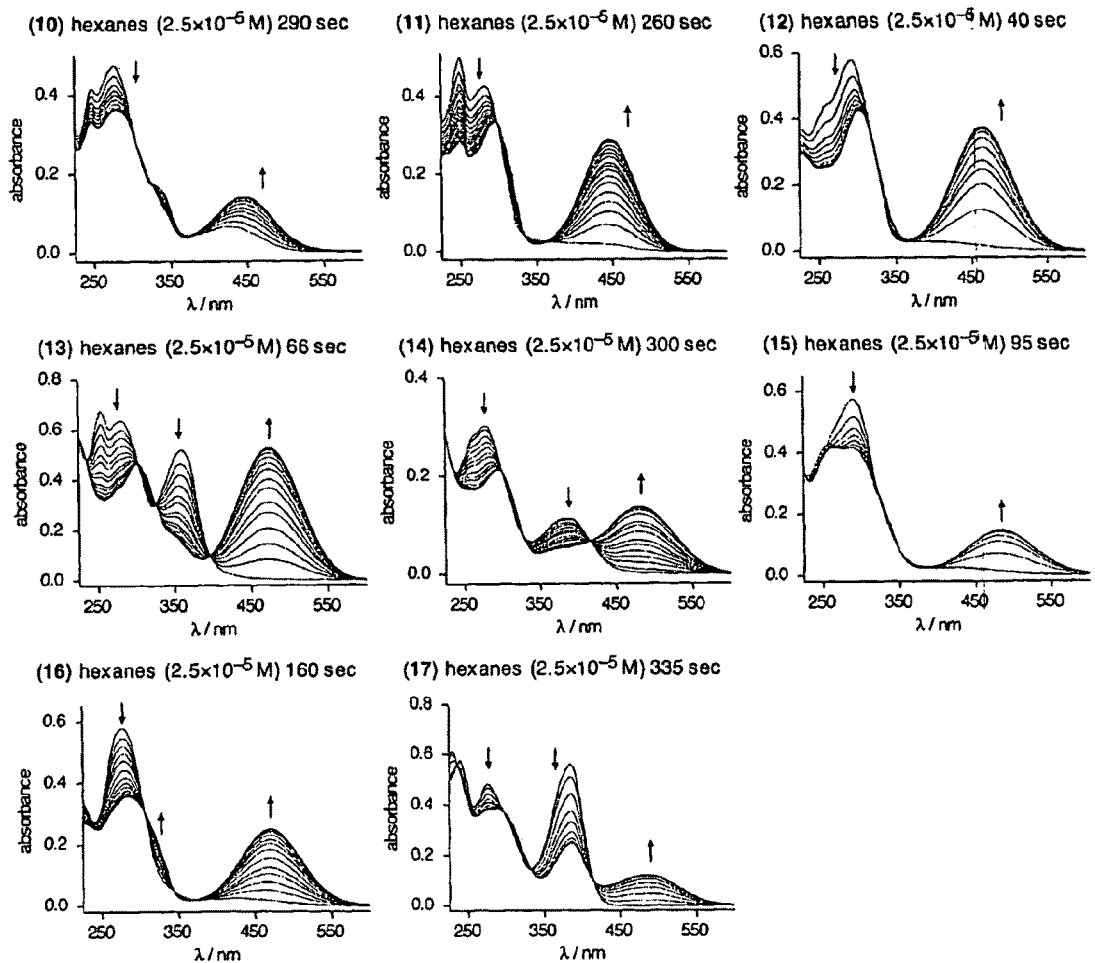
FIG. 1 are graphs showing changes in the UV-VIS absorption spectra of solutions of compounds 10-17 when irradiated with 365-nm light (313 nm for 12). The solvent, concentrations and total irradiation times for each compound are provided in the figure.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

General Chemical Structure of Isomeric Hexatriene Compounds

This application relates to hexatriene compounds and methods of synthesizing and using same. As shown in Scheme 1 below, each compound of the invention is reversibly convertible between a ring-open isomeric form I(o) and a ring-closed isomeric form I(c):

Scheme 1

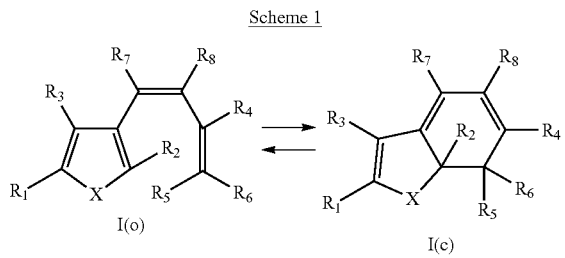

As described further below, the conversion between the isomeric forms I(o) and I(c) may be triggered by light and/or an electrical stimuli. For example, conversion from the ring-open form to the ring-closed form may be triggered by ultraviolet light and conversion from the ring-closed form to the ring-open form may be triggered by visible light.

The $R_1$-$R_8$ substituents of compound (I) may vary without departing from the invention. For example, X may be a heteroatom such as S, N and O; $R_1$ may be H, a halogen, alkyl, aryl and substituted aryl; $R_2$ may be alkyl, aryl and substituted aryl; $R_3$ may be H and alkyl; $R_4$ may be H, alkyl, aryl, substituted aryl, an electron-donating group, an electron-accepting group, and an optionally substituted constituent of a heterocycle; $R_5$ may be alkyl, aryl, substituted aryl, an electron-donating group and an electron-accepting group; $R_6$ may be alkyl, aryl, substituted aryl, an electron-donating group, an electron-accepting group and an optionally substituted constituent of a heterocycle; and $R_7$ and $R_8$ may be a constituent of a 5 membered ring comprising H or a halogen or an optionally substituted 6 membered ring. In a particular embodiment where $R_4$ and $R_6$ are constituents of a thiophene ring and $R_5$ is an alkyl, aryl or substituted aryl, then $R_7$ and $R_8$ are constituents of an optionally substituted 6 membered ring. In another embodiment where $R_7$ and $R_8$ are constituents of a 5 membered halogenated ring, then $R_4$, $R_5$ and $R_6$ are independently not an alkyl or aryl.

Charge Transfer Moiety

As indicated above, substituents $R_4$-$R_6$ may optionally include electron-donating and electron-accepting groups. This feature is described more fully in the generalized structures shown in Schemes 2 and 3 below. In this embodiment of the invention, charge transfer between the electron-donating group(s) 'D' and the electron-accepting group(s) 'A' is regulated by photo-induced switching of the hexatriene compound between the ring-open and ring-closed isomeric forms.

Scheme 2

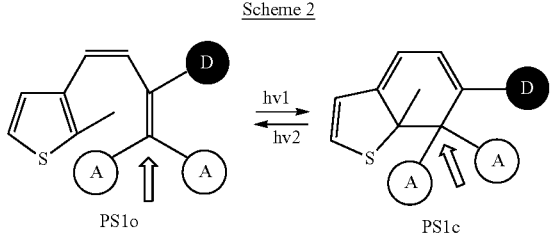

Scheme 3

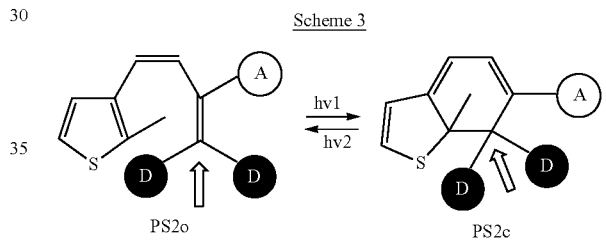

With reference to Schemes 1 and 2, $R_4$ may be an electron-donating group 'D' and $R_5$ and $R_6$ may be electron-accepting groups 'A'. Only in the ring-open isomer (PS1o) are the 'D' and 'A' groups electronically connected to each other by an alkene creating a D-π-A motif. In the ring-closed isomer (PS1c), the 'A' and 'D' groups are electronically insulated from each other and the D-π-A motif has been removed. Similarly, with reference to Schemes 1 and 3, $R_4$ may be an electron-accepting group 'A' and $R_5$ and $R_6$ may be electron-donating groups 'D'. Only in the ring-open isomer (PS2o) are the 'D' and 'A' groups electronically connected to each other by an alkene creating a D-π-A motif. In the ring-closed isomer (PS2c), the 'A' and 'D' groups are electronically insulated from each other and the D-π-A motif has been removed. In both examples the ring-closing reaction triggered by irradiation with a particular wavelength of light (hv1) causes a change in hybridization of one of the carbons (highlighted by the arrows in Schemes 2 and 3 above) connecting the donating group to the accepting group thus resulting in the break in the linear π-conjugation. The reverse reaction and the reconstruction of the D-π-A motif can be triggered by a different wavelength of light (hv2).

The installation of electron donor and acceptor groups at the ends of a linear π backblone in the ring-open embodiment creates an asymmetric charge distribution. As mentioned above, structures having a polarisable π-conjugated framework may be suitable for NLO applications. The photo-switching of the donor-π-acceptor systems has the potential to significantly impact opto-electronic, electro-optic and photonic devices and materials.

As described further below, the invention encompasses synthetic methods for spatially installing different donor and acceptor groups on the photoresponsive hexatriene backbone. For example, with reference to Scheme 2, donor 'D' on PS1o and PS1c may include alkyl groups or aromatic rings bearing electron-donor substituents (such as phenols, phenol ethers and anilines) or electron-donating heterocycles (such as thiophenes). Suitable acceptor groups 'A' on PS1o and PS1c could include carbonyl-based functional groups such as nitriles (CN). With reference to Scheme 3, donor 'D' on PS2o and PS2c may include electron-donating sulfides and acceptor 'A' may include aromatic rings bearing electron-withdrawing substituents (such as nitrobenzene) and heterocycles (such as pyridine). According to one synthetic scheme, hexatriene compounds comprising a charge transfer moiety including an electron donor and acceptor may be derived from the condensation of thiophene-functionalized aldehydes or ketones with activated methylene compounds or with ylides. Such carbonyl synthons offer a wide range of possible synthetic modifications and hence a large variety of electron donor and acceptor groups can be installed on the same structural backbone. The result is a convenient and modular method to produce numerous "made-to-order" photoresponsive materials from the same set of starting materials.

The general molecular architecture and synthetic route is particularly appealing since the D-π-A motif is positioned at the side of the hexatriene unit, which allows for the greatest amount of flexibility and tolerance in preparation and derivatization. Other photoresponsive D-π-A motifs based on dithienylethenes bear the donor and acceptor groups on the thiophene rings. This is less appealing since it limits how the molecule may be decorated with useful groups which impart the desired properties.

Pentene Ring Embodiment

Scheme 4 illustrates a particular embodiment of the invention where $R_7$ and $R_8$ (as shown generally in Scheme 1 above) together comprise a pentene ring.

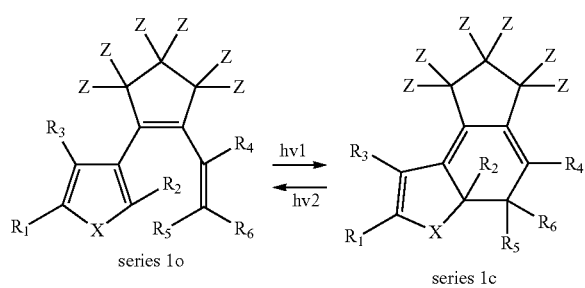

Scheme 4

In this example the Z substituents of the pentene ring may either be H or a halogen, such as fluorine. As in the other embodiments of the invention, the hexatriene compound is reversibly convertible between the ring-open and ring-closed isomeric forms by a light trigger, such as UV light and visible light. The wavelengths of light acting as conversion triggers may vary and may be "tuned" by decorating the molecular background with different functional groups.

Reactivity-Gated Photochromism and Electrochromisim

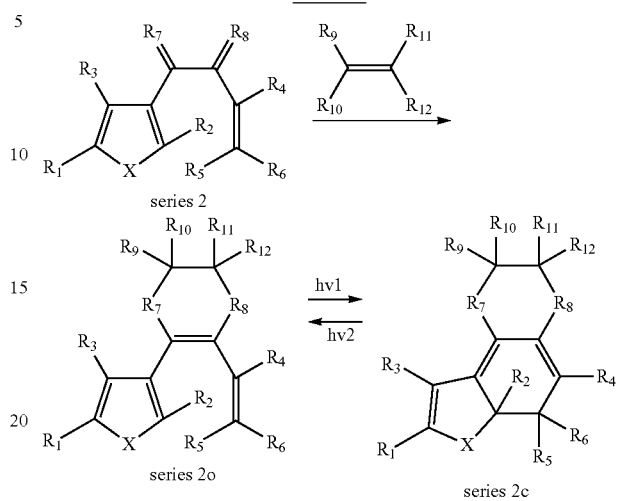

Scheme 5

Scheme 5 illustrates a representative process for producing a photoresponsive hexatriene compound of the invention from a condensation reaction between a diene precursor and a dienophile. In this example, the precursor is a butadiene and the dienophile is an alkene. The particular condensation reaction shown is a cycloaddition. The condensation reaction may, for example, consist of Diels-Alder [4+2]cycloaddition with the dienophile(s). As will be apparent to a person skilled in the art, many variations are possible without departing from the invention. According to the embodiment of Scheme 5, the initial butadiene is photochemically inert (i.e. it does not undergo a facile photoreaction). The butadiene precursor undergoes a thermally induced condensation reaction to produce a photoresponsive hexatriene reversibly convertible between different isometric forms as discussed above. The optical and electronic differences between the ring-open and ring-closed isomers can be used as a read-out signal to sense the presence of the dienophile and its dose. In this example the $R_9$, $R_{10}$, $R_{11}$ and $R_{12}$ substituents of the alkene may include H, alkyl, aryl, CN, $CO_2$-alkyl, $CO_2$-aryl, anhydride and imide.

Scheme 5 is an example of reactivity-gated photochromic system. That is, irradiation of the system with light does not trigger a molecular transformation unless another external "gate" stimulus, in this case a thermally induced condensation reaction, occurs prior to or during the irradiation period. As discussed above, in reactivity-gated photochromism or electrochromism, an initial chemical reaction must occur to convert the compound from a non-photo or non-electroactive state to a photo or electroactive state. Only after this initial reaction takes place can the compounds be photochemically interconverted between two isomers displaying unique properties such as, but not limited to, the absorption and emission of light, refractive index and other optical properties, redox properties, and topological properties.

Further with reference to Scheme 5, when the groups labeled '$R_4$' and '$R_6$' make up a heterocycle, such as a thiophene ring, the compounds resemble the dithienylethenes that are known to undergo photo- and electrochromic reactions and can be reversibly converted between their ring-open (series 2o) and ring-closed (series 2c) forms. Each isomer possesses unique properties already described for other photochromic compounds. This provides a variety of output signals that can be detected (e.g. color, redox potential, dipole moment, host-guest chemistry).

This technological approach is general and can be applied to a wide range of architectures as long as they are photostable and undergo mild reactions to produce photoactive hexatriene architectures. For example, when the groups labeled as '$R_7$' and '$R_8$' in Scheme 5 are carbon, a wide variety of electrocyclization reactions are possible. These groups can also be a part of a cyclic or acyclic conjugated system. As will be apparent to a person skilled in the art, these compounds can be subjected to polymerization reactions to produce functional materials such as conjugated polymers. When they are a part of a pentadiene system, they may be deprotonated and undergo condensation reactions with other carbonyl compounds to produce novel butadienes as illustrated in Scheme 6, below, providing access to new methods to decorate these photo- and electro-responsive compounds with functionality.

Scheme 6

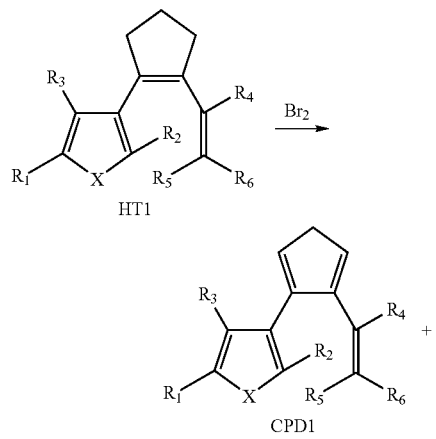

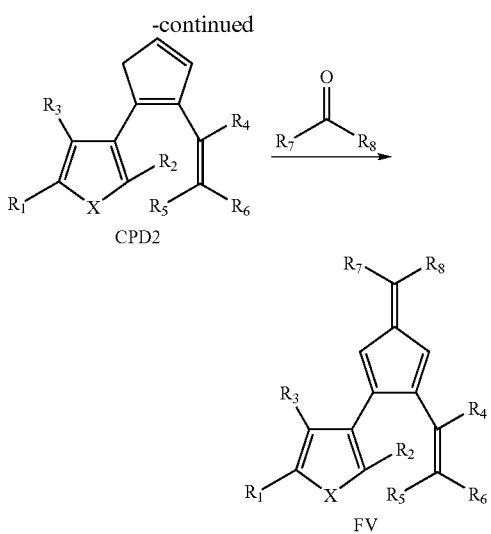

The final product (FV) of the reactions of Scheme 6 is a fulvene. Fulvene FV may be prepared in a "one-pot" procedure without the need to isolate the cyclopentadiene intermediates (CPD1 and CPD2). In this embodiment the general synthetic scheme involves reacting the initial hexatriene (HT1) with bromine. The reaction product undergoes spontaneous elimination to generate a mixture of cyclopentadienes (CPD1 and CPD2). The cyclopentadienes may be condensed with aldehydes and ketones to generate the final fulvenes FV. In this example $R_7$ and $R_8$ may comprise H, alkyl, substituted alkyl, aryl and substituted aryl.

Selective Release of Reactants

Scheme 7 illustrates one particular application of the reactivity-gated concept described above to achieve controlled release of a "releasable agent" or other reactant. In this example, the releasable agent is a dienophile, namely an alkene.

Scheme 7

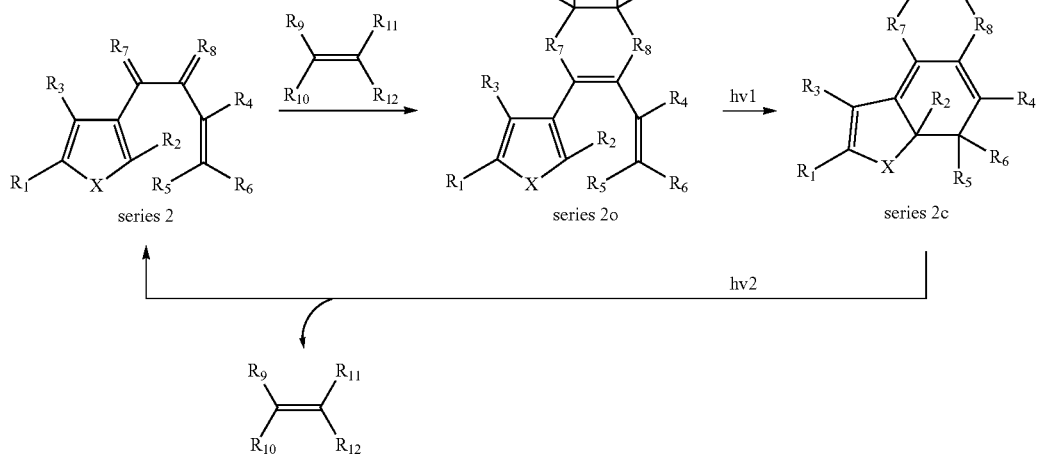

The butadiene precursor (series 2) undergoes thermally induced condensation reactions with alkenes to generate photoresponsive hexatrienes (series 2o). These ring-open isomers can be transformed into their ring-closed counterparts (series 2c) when irradiated with UV light. The ring-closed isomers are thermally stable and cannot undergo the thermal back reaction. The light effectively "locks" the thermal reaction. The reverse photochemical reaction can be induced with visible light. This "unlocks" the system and allows for the spontaneous thermal release of the alkene. This embodiment relies on the fact that the ring-open form of the hexatriene is unstable and the condensation reaction is reversible. The thermally unstable compound spontaneously fragments to liberate the alkene or other releasable agent(s).

The structure of the "locked" forms of the molecule can be synthetically modified so that different wavelengths of light can trigger the release of different compounds providing a means to selectively release one compound in the presence of others. Also, the differences in optical and electronic properties of the "locked" and released forms of the compounds provides a means to monitor the spacial and temporal release of the compounds. This will be useful for the delivery of releasable agents such as therapeutics, biochemical effectors, polymer precursors, biorelevant molecules and chemical reagents for photolithography and for locking thermally reversible polymerization processes.

This embodiment of the invention offers a universal photorelease approach where the electronic properties of the chromophore (series 2c) can be fine-tuned by tailoring the photoresponsive scaffold without negatively affecting the performance of the system. This embodiment is adaptable to many chemistries and environments, and can be applied to many different substrates and many different situations. It also offers a means to selectively and sequentially release different species using light of different wavelengths. Because the "locked" compounds absorb long-wavelength light, cellular damage is minimized. The molecular system is also easily derivatized using synthetic methods that are tolerant to a wide range of chemistries. This controlled photorelease approach may be useful for drug delivery and photodynamic therapy applications.

The technology extends far beyond the discharge of molecules selectively with a high degree of temporal and spatial control. Because the two derivatives (series 2) and (series 2c) exhibit a wide range of properties unique to their structures, the technology offers a means to "release and report" to quantify the extent and location of discharge by monitoring an optical or electronic read-out signal including, but not limited to, color, refractive index, luminescence and redox chemistry.

Applications

In one embodiment the invention involves the reversible connection and insulation of two functional groups at each end of a conjugated pathway and the use of reactivity-gated switching to provide an additional means to regulate this concept. The result is that any application that benefits from this connection/disconnection mechanism will potentially be impacted. This includes, but is not limited to, optoelectronics (optical filters, data storage), electro-optics (waveguides), health sciences (drug release and photodynamic therapy) and chemical reactivity (catalysis and reagents).

As indicated above, linear conjugation within D-π-A systems often results in significant polarization of the molecule and is the basis for numerous useful and important materials properties such as refractive index, non-linear optical properties and the absorption/reflection of light. Photoregulating these properties will impact many optoelectronic, electrooptic and photonic applications such as waveguides, reflectors, filters and dyes.

In one embodiment of the invention the hexatriene compound may bear a phenol group at the position labeled $R_4$ (Scheme 1). This embodiment structurally resembles tyrphostins, which have shown potential as protein tyrosine kinase (PTK) inhibitors. The ability of kinases to influence the growth and progression of proliferative conditions has made them attractive targets for new chemotherapeutics, including small molecule inhibitor drugs that specifically target kinases known to be deregulated in cancers. Acting as signal blockers, tyrphostins are a promising class of inhibitors that has proven to be effective at inhibiting the growth of tumor cell lines and in vivo tumors. The tyrphostins share a common dehydrated tyrosine sub-structure as shown by the hydroxy-benzylidene-malonodinitriles (e.g. AG17) and hydroxy-benzylidene-cyclopentendione (e.g. KIH and TX) series. As will be apparent to a person skilled in the art, the functional groups of the compounds of the invention may be tailored to mimic, inhibit or otherwise regulate biological active molecules.

Other important examples include those that have acidic, basic or nucleophilic groups as the 'A' or 'D' groups. In these cases, the connection through the linear π-system results in the increase or decrease (depending on the example) of the reactivity of the particular group. Photo- or electrocyclization reverses the response. This provides a versatile means to photo- or electromodulate chemical reactivity on command and has the potential to significantly influence catalysis and chemical processing.

The concept of reactivity-gated photochromism and electrochromism has the potential to significantly impact numerous applications. It can be applied to sensing and dosiometry applications, taking advantage of the wide range of output signals offered by the systems (e.g. absorption, emission, redox). It can be applied to controlled release systems (e.g. drug delivery) and to the tuning of the mechanical properties of polymers. The compounds described here provide access to novel methods to prepare photochromic and electrochromic compounds. They also provide access to novel monomers for the preparation of functional polymers.

EXAMPLES

The following examples are intended to illustrate embodiments of the invention and are not intended to be construed in a limiting manner.

Experimental

Materials

All solvents used for synthesis and UV-VIS absorption spectroscopy were dried by passing them through steel columns containing activated alumina under nitrogen using an MBraun solvent purification system. Solvents for NMR analysis were purchased from Cambridge Isotope Laboratories and used as received. Column chromatography was performed using silica gel 60 (230-400 mesh) from Silicycle Inc. and solvents purchased from Aldrich that were used as received. The starting materials, 2-fluoro-1-(2'-methyl-5'-phenylthien-3'-yl)hexafluorocyclopentene (1) [7]. 1,2-bis(2,5-dimethyl-3-thienyl)ethanedione (23) [8] and 1,4-butanebis (triphenylphosphonium)dibromide [9], 1,2-bis(5'-phenyl-2'-methylthieny-3'-yl)cyclopentene (28) [10], 1,2-bis(5'-chloro-2'-methylthieny-3'-yl)cyclopentene (29) [11] and diethyl dicyanofumarate [12] were prepared as described in the literature. All other reagents and starting materials were purchased from Aldrich.

7 Peters, A.; Vitols, C.; McDonald, R.; Branda, N. R. *Org. Lett.* 2003, 5, 1183.
8 Ivanov, S. N.; Litchitskii, B. V.; Martynkin, A. Y.; Krayushkin, M. M. *Chem. Heterocycl. Comp.* 2001, 37, 85.
9 Calcagno, P.; Kariuki, B. M.; Kitchin, S. J.; Robinson, J. M. A.; Philip, D.; Harris, K. D. M. *Chem. Eur. J.* 2000, 6, 2338.
10 de Jong, J. J. D.; Lucas, L. N.; Hania, R.; Pugzlys, A. Feringa, B. L.; Duppen, K.; van Esch, J. H. Eur. *J. Org. Chem.* 2003, 1887.
11 Lucas, L. N. van Esch, J. H.; Kellogg, R. M.; Feringa, B. L. *Chem. Commun.* 1998, 2313.
12 Ireland, C. J.; Jones, K.; Pizey, J. S.; Johnson, S. *Synth. Commun.* 1976, 6, 185.

Instrumentation $^1$H NMR characterizations were performed on a Varian INOVA 500 working at 499.770 MHz or a Bruker AMX 400 instrument working at 400.103 MHz. $^{13}$C NMR characterizations were performed on a Bruker AMX 400 instrument working at 100.610 MHz. $^{19}$F NMR characterizations were performed on a Varian Inova 500 instrument. Chemical shifts (δ) are reported in parts per million relative to tetramethylsilane using the residual solvent peak as a reference standard. $^{19}$F NMR spectra were referenced against BrCH$_2$BrCF$_2$ (−52.1 ppm). Coupling constants (1) are reported in hertz. FT-IR measurements were performed using a Nicolet Nexus 670 instrument, UV-VIS absorption spectroscopy was performed using a Varian Cary 300. Bio spectrophotometer. Exact mass measurements were done using a Kratos Concept-H instrument with perfluorokerosene as the standard.

Photochemistry

All ring-closing reactions were carried out using the light source from a lamp used for visualizing TLC plates at 313 nm or 365 nm(Spectroline E-series, 470 W/cm$^2$). The ring-opening reactions were carried out using the light of a 300-W halogen photo optic source passed through appropriate cutoff filters to eliminate higher energy light. The selective ring-opening reactions were carried out using the light source (75 W xenon lamp) from a PTI QM-2000-4 scanning spectrofluorimeter.

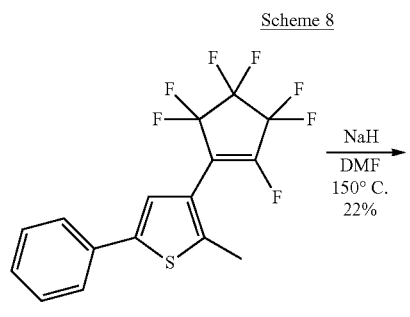

Scheme 8

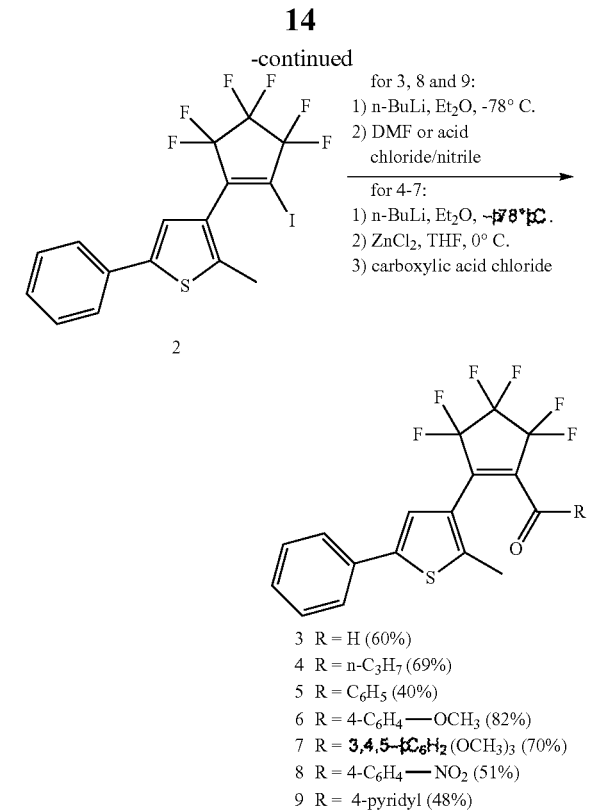

3 R = H (60%)
4 R = n-C$_3$H$_7$ (69%)
5 R = C$_6$H$_5$ (40%)
6 R = 4-C$_6$H$_4$—OCH$_3$ (82%)
7 R = 3,4,5-C$_6$H$_2$(OCH$_3$)$_3$ (70%)
8 R = 4-C$_6$H$_4$—NO$_2$ (51%)
9 R = 4-pyridyl (48%)

Synthesis of Iodoperfluorocyclopentene 2

A solution of heptafluorocyclopentene 1 (680 mg, 1.84 mmol) and anhydrous sodium iodide (560 mg, 3.52 mmol) in anhydrous DMF (4 mL) was placed in a nitrogen flushed 10 mL pyrex tube equipped with a magnetic stir bar. The tube was sealed and the solution was heated to 150° C. in an oil bath for 6 h and then stirred at room temperature overnight. The solution was diluted with diethyl ether (100 mL) and washed with water (4×15 mL). The organic layer was dried over MgSO$_4$, filtered and the solvents were removed under reduced pressure. Purification by column chromatography (SiO$_2$, hexanes) afforded 189 mg (22%) of the compound 2 as a white solid. Mp=74° C.; $^1$H NMR (CDCl$_3$): δ=2.46 (s, 3H), 7.10 (s, 1H), 7.31 (m, 1H), 7.39 (m, 2H), 7.55 (m, 2H); $^{13}$C NMR (CDCl$_3$): δ=15.3, 122.2, 125.9, 128.2, 129.2, 133.5, 140.6, 142.8; MS (CI): 475 (M$^+$).

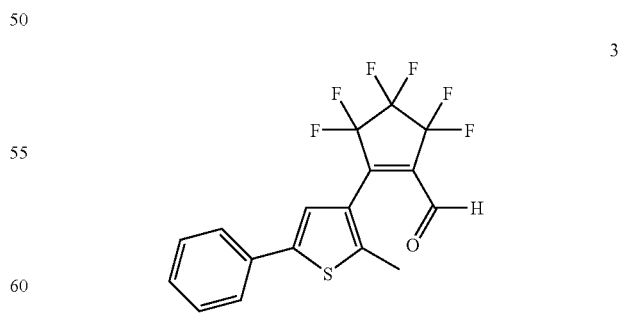

Synthesis of Aldehyde 3

A solution of iodide 2 (200 mg, 0.42 mmol) in anhydrous Et$_2$O (25 mL) was cooled in an acetone/dry-ice bath to −78°

C. and treated with n-BuLi (170 μL, 2.5 M in hexane, 0.42 mmol) in one portion via a syringe. The resulting yellow solution was stirred for 15 min at −78° C. before anhydrous DMF (97 μA 1.26 mmol) was added. After stirring for another 10 min, the reaction was quenched with saturated aqueous NH$_4$Cl and the cooling bath was removed. The two layers were allowed to warm to room temperature, separated and the aqueous phase was extracted with Et$_2$O (3×20 mL). The combined organic extracts were dried over MgSO$_4$, filtered and concentrated under reduced pressure. Purification by column chromatography (SiO$_2$, hexane/ethyl acetate 6:1) afforded 95 mg of compound 3 (60%) as a yellow solid. Mp 89-91° C.; $^1$H NMR (CD$_2$Cl$_2$): δ=2.50 (s, 3H), 7.31 (s, 1H), 7.37 (m, 1H), 7.44 (m, 2H), 7.60 (m, 2H), 9.77 (s, 1H); $^{13}$C NMR (CDCl$_3$): δ=14.7, 122.7, 126.0, 128.7, 129.3, 132.8, 143.8, 145.6, 184.8; MS (CI): 377 (M$^+$).

Synthesis of Ketones 4-7

In a 25 mL three-necked flask, compound 2 (200 mg, 0.42 mmol) was dissolved in anhydrous Et$_2$O (8 mL). The solution was cooled to −78° C. under a nitrogen atmosphere and treated with n-BuLi (186 μL, 2.5 M in hexane, 0.46 mmol) in one portion. After stirring for 15 min at this temperature, a solution of anhydrous zinc chloride (64 mg, 0.46 mmol) in anhydrous THF (0.8 mL) was added drop-wise. The acetone/dry-ice bath was exchanged with an ice bath and after stirring for further 30 min, all solvents were removed under reduced pressure. The resulting residue was dissolved in anhydrous THF (0.5 mL), cooled to 0° C. and treated with the appropriate carboxylic acid chloride (0.5 mmol), followed by a catalyst solution (0.5 mL) prepared from [Pd(PPh$_3$)$_2$]Cl$_2$ (21 mg) and i-Bu$_2$AlH (36 mL, 1.5 M in toluene) dissolved in anhydrous benzene (1 mL). Stirring was continued for 30 min at which time the ice-bath was removed and the dark red solution was stirred overnight at room temperature. After quenching with 1N aqueous HCl, the mixture was extracted with hexane (3×20 mL). The organic extracts were washed with saturated NaHCO$_3$, dried with brine and MgSO$_4$, filtered and the solvents were evaporated under reduced pressure.

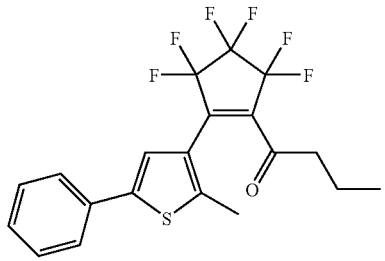

(4) Prepared from n-butanoyl chloride and purified by column chromatography (SiO$_2$, 10:1 hexane/ethyl acetate gradient) as a yellow solid in 69% yield (121 mg). Mp=67-68° C.; $^1$H NMR (CDCl$_3$): δ=0.85 (t, J=7.0 Hz, 3H), 1.59 (tq, J=7.0, 7.0 Hz, 2H), 2.34 (s, 3H), 2.50 (t, J=7.0 Hz, 2H), 7.15 (s, 1H), 7.32 (m, 1H), 7.40 (m, 2H), 7.55 (m, 2H); $^{13}$C NMR (CDCl$_3$): δ=13.6, 14.6, 16.8, 44.7, 122.4, 124.2, 125.9, 128.4, 129.3, 133.2, 142.5, 143.1, 196.2; MS (CI): 419 (M$^+$).

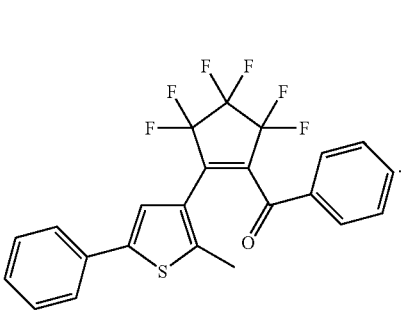

(5) Prepared from benzoyl chloride and purified by column chromatography (SiO$_2$, 10:1 hexane/ethyl acetate) as a yellow solid in 40% yield (78 mg). Mp=70-73° C.; $^1$H NMR (CDCl$_3$): δ=2.29 (s, 3H), 7.11 (s, 1H), 7.29 (m, 1H), 7.36 (m, 4H), 7.42 (m, 2H), 7.53 (m, 1H), 7.73 (m, 2H); MS (CI): 453 (M$^+$).

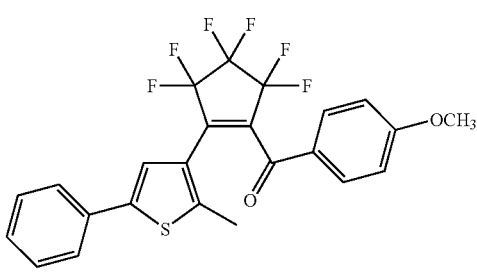

(6) Prepared from 4-methoxybenzoyl chloride and purified by column chromatography (SiO$_2$, hexane/ethyl acetate 5:1) and recrystallization from hexane as a yellow solid in 82% yield (87 mg). Mp=87-89° C.; $^1$H NMR (CDCl$_3$): δ=2.31 (s, 3H), 3.81 (s, 3H), 6.84 (m, 2H), 7.13 (s, 1H), 7.28 (m, 1H), 7.35 (m, 2H), 7.44 (m, 2H), 7.73 (m, 2H); $^{13}$C NMR (CDCl$_3$): δ=14.8, 55.8, 114.4, 122.6, 124.4, 125.8, 128.1, 128.2, 129.2, 132.0, 133.3, 142.8, 143.0, 165.2, 186.9; MS (CI): 483 (M$^+$).

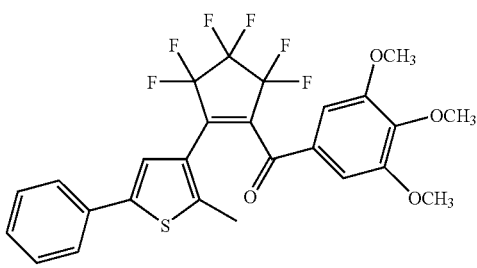

(7) Prepared from compound 2 (250 mg, 0.53 mmol), n-BuLi (240 μL, 2.5 M in hexane, 0.59 mmol), zinc chloride (80 mg, 0.58 mmol) and 3,4,5-trimethoxybenzoyl chloride (0.5 mmol). The product was purified by column chromatography (SiO$_2$, 5:1 hexane/ethyl acetate) as a yellow solid in 70% yield (200 mg). Mp=111-112° C.; $^1$H NMR (CDCl$_3$): δ=2.33 (s, 3H), 3.82 (s, 6H), 3.88 (s, 3H), 7.02 (s, 2H), 7.14 (s, 1H), 7.30 (m, 1H), 7.36 (m, 2H), 7.43 (m, 2H); $^{13}$C NMR (CDCl$_3$): δ=14.8, 56.4, 61.2, 107.1, 122.4, 125.7, 128.4, 129.2, 129.8, 133.0, 143.1, 143.2, 144.7, 153.3, 187.2; MS (CI): 543 (M$^+$).

8

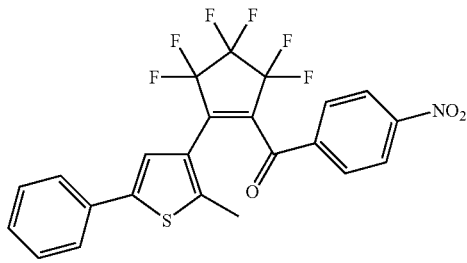

Synthesis of Ketone 8

A solution of iodide 2 (200 mg, 0.42 mmol) in anhydrous Et$_2$O (8 mL) was cooled to −78° C. under a nitrogen atmosphere and treated with n-BuLi (1.86 mL, 2.5 M in hexane, 0.46 mmol) in one portion. After stirring for 15 min at this temperature, 4-nitrobenzoyl chloride (78 mg, 0.42 mmol) was added. The resulting green solution was stirred at −78° C. for 1 h, the acetone/dry-ice bath was removed and the solution was allowed to warm to room temperature, during which time a colour changed from yellow to reddish brown. The solvent was removed under reduced pressure and the resulting residue was transferred to a silica column (SiO$_2$, hexanes/ethyl acetate 11:1). Purification by column chromatography afforded 107 mg (51%) of ketone 8 as a yellow solid. Mp=95-97° C.; $^1$H NMR (CDCl$_3$): δ=2.27 (s, 3H), 7.11 (s, 1H), 7.31 (m, 1H), 7.37 (m, 2H), 7.40 (m, 2H); $^{13}$C NMR (CDCl$_3$): δ=14.7, 122.0, 124.2, 125.9, 128.6, 129.3, 130.1, 132.7, 139.3, 143.7, 144.0, 151.2, 187.7; MS (CI): 498 (M$^+$).

9

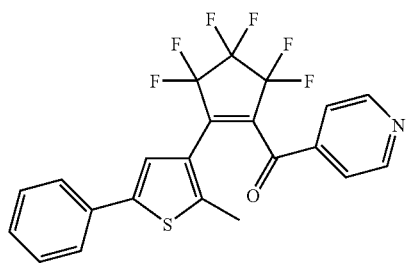

Synthesis of Ketone 9

A solution of iodide 2 (200 mg, 0.42 mmol) was dissolved in anhydrous Et$_2$O (8 mL). The solution was cooled to −78° C. under a nitrogen atmosphere and treated with n-BuLi (1.86 mL, 2.5 M in hexane, 0.46 mmol) in one portion. After stirring for 15 min at this temperature, 4-cyanopyridine (44 mg, 0.42 mmol) was added. The orange solution was stirred at −78° C. for further 20 min, at which time the acetone/dry-ice bath was exchanged with an ice-bath. Stirring was continued for an additional 15 min before the brown solution was acidified with 6 N HCl to pH 1. After 1 h, the pH was adjusted to 10 by addition of solid KOH while cooling with ice. The mixture was extracted with ethyl acetate and the extracts were dried over MgSO$_4$. The solvent was removed in vacuum. The resulting dark brown oil was transferred to a column (SiO$_2$, hexanes/ethyl acetate 5:1) and purified by column chromatography to afford 91 mg (48%) of ketone 9 as a yellow solid. $^1$H NMR (CDCl$_3$): δ=2.25 (s, 3H), 7.10 (s, 1H), 7.31 (m, 1H), 7.37 (m, 2H), 7.42 (m, 2H), 7.49 (br s, 2H), 8.72 (br s, 2H); $^{13}$C NMR (CDCl$_3$): δ=14.7, 122.1, 124.3, 126.0, 128.7, 129.3, 132.7, 140.9, 143.8, 144.0, 151.1, 188.8; MS (CI): 454 (M$^+$).

Scheme 9

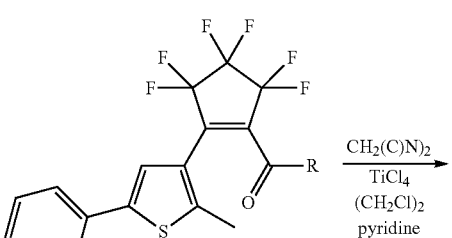

3-9

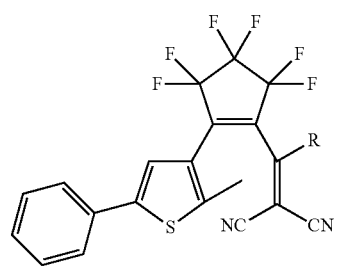

10 R = H (93%)
11 R = n-C$_3$H$_7$ (83%)
12 R = C$_6$H$_5$ (74%)
13 R = 4-C$_6$H$_4$—OCH$_3$ (36%)
14 R = 3,4,5-ʙ C$_6$H$_2$(OCH$_3$)$_3$ (26%)
15 R = 4-C$_6$H$_4$—NO$_2$ (62%)
16 R = 4-pyridyl (83%)

Synthesis of Compounds 10-15

A solution of aldehyde 3 or the appropriate ketone 4-9 (0.1 mmol) and malonodinitrile (16.5 mg, 0.25 mmol) in anhydrous dichloroethane (5 mL) was cooled in an ice bath to 0° C. under nitrogen atmosphere and treated with TiCl$_4$ (0.1 ml, 0.91 mmol) drop-wise. After stirring for 5 min, pyridine (0.2 mL) was carefully added over 20 min. The purple reaction mixture was allowed to warm to room temperature and subsequently heated at reflux for 5-10 min during which time a white precipitate formed and the colour changed to pale brown. After cooling to room temperature, the solvents were evaporated under reduced pressure. The solid residue was dissolved in 15% aqueous HCl (10 mL), the solution was extracted with CHCl$_3$ (3×20 mL) and the combined organic layers were dried over MgSO$_4$, filtered and concentrated in vacuum. Purification of the crude product affords compounds 10-15

10

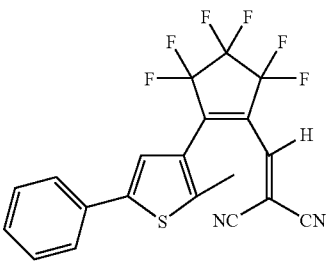

(10) Prepared from aldehyde 3 in 93% yield (40 mg) as an orange solid. $^1$H-NMR spectroscopy indicated the product was pure enough to use without further purification. Mp=102-104° C.; NMR (CDCl$_3$): δ=2.40 (s, 3H), 7.18, 7.21 (2s, 2×1H), 7.36 (m, 1H), 7.42 (m, 2H), 7.55 (m, 2H); $^{13}$C NMR (CDCl$_3$): δ=15.3, 92.6, 109.9, 112.6, 122.3, 124.4, 126.2, 129.0, 129.4, 132.5, 144.8, 145.3; $^{19}$F NMR (CDCl$_3$): δ=108.55, −113.49, −133.51; MS (CI): 425 (M$^+$); Anal Calcd. C 56.61; H, 2.38; N, 6.60. Found: C, 56.32; H, 2.50; N, 6.77.

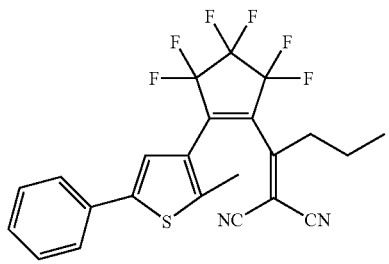

11

(11) Prepared from ketone 4 and purified by column chromatography (SiO$_2$, hexane/ethyl acetate 10:1) on a short silica plug (2.5 cmØ×4 cm) as an orange-yellow oil in 83% yield (39 mg). $^1$H NMR (CDCl$_3$): δ=1.03 (t, J=7.0 Hz, 3H), 1.66 (tq, J=7.0, 7.0 Hz, 2H), 2.45 (s, 3H), 2.70 (m, 2H), 7.03 (s, 1H), 7.34 (m, 1H), 7.41 (m, 2H), 7.52 (m, 2H); $^{13}$C NMR (CDCl$_3$): δ=14.2, 15.2, 21.7, 38.3, 93.0, 110.7, 123.2, 122.8, 126.0, 128.6, 129.4, 132.9, 142.6, 143.8, 167.4; $^{19}$F NMR (CDCl$_3$): δ=−110.02, −113.37, −134.36; MS (CI): 467 (M$^+$); Anal Calcd. C, 59.22; H, 3.46; N, 6.01. Found: C, 59.08; H, 3.63; N, 6.20.

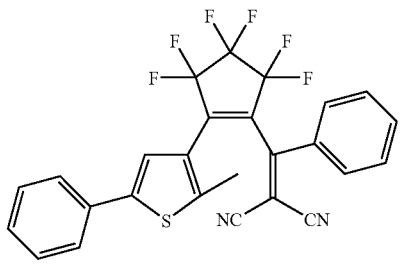

12

(12) Prepared from ketone 5 and purified by column chromatography (SiO$_2$, hexane/ethyl acetate 10:1) as an yellow solid in 74% yield (39 mg). Mp=110-111° C.; $^1$H NMR (CDCl$_3$): δ=2.43 (s, 3H), 6.88 (s, 1H), 7.32 (m, 1H), 7.37 (m, 2H), 7.41 (m, 2H), 7.55 (m, 2H, ar CH), 7.63 (m, 3H, ar CH); $^{13}$C NMR (CDCl$_3$): δ=15.1, 88.8, 111.9, 112.1, 122.5, 123.3, 125.9, 128.5, 129.3, 129.4, 129.8, 132.1, 132.9, 134.2, 143.2, 143.5, 161.2; $^{19}$F NMR (CDCl$_3$): δ=−109.53, −113.52, −134.72; MS (CI): 501 (M$^+$); Anal Calcd. C, 62.40; H, 2.82; N, 5.60. Found: C, 62.16; H, 3.01; N, 5.30.

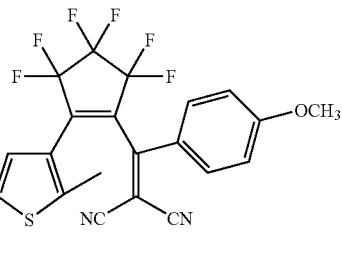

13

(13) Prepared from ketone 6 and purified by column chromatography (SiO$_2$, hexane/ethyl acetate 10:1) as an orange oil in 36% yield (19 mg). $^1$H NMR (CDCl$_3$): δ=2.45 (s, 3H), 3.89 (s, 3H), 6.87 (s, 1H), 7.02 (m, 2H), 7.29 (m, 1H), 7.36 (m, 4H), 7.70 (m, 2H); $^{13}$C NMR (CDCl$_3$): δ=15.3, 56.1, 84.5, 112.6, 113.0, 114.8, 115.3, 122.7, 123.2, 124.0, 125.9, 128.4, 129.3, 129.9, 132.2, 133.0, 143.1, 143.2, 159.5, 164.7; $^{19}$F NMR (CDCl$_3$): δ=−110.13, −113.37, −134.79; MS (CI): 531 (M$^+$); Anal Calcd. C, 61.13; H, 3.04; N, 5.28. Found: C, 61.34; H, 3.02; N, 5.10.

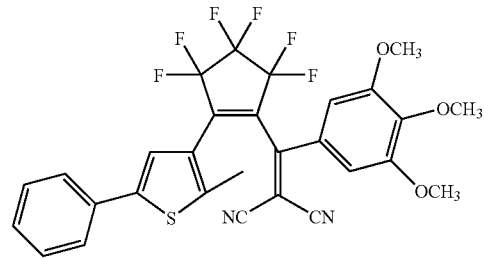

14

(14) Prepared from ketone 7 (0.25 mmol), malanodinitrile (0.68 mmol), TiCl$_4$ (2.28 mmol) and pyridine (0.5 mL). The product was purified by column chromatography (SiO$_2$, 4:1 hexane/acetone) on a long silica column (2.5 cm Ø×80 cm) as an orange oil in 26% yield (39 mg). $^1$H NMR (CDCl$_3$): δ=2.46 (s, 3H), 3.85 (s, 6H), 3.96 (s, 3H), 6.84 (s, 1H), 6.92 (s, 2H), 7.32 (m, 1H), 7.37 (m, 4H); $^{13}$C NMR (CDCl$_3$, 125 MHz): δ=159.9, 153.5, 143.9, 143.4, 143.1, 132.8, 129.4, 128.6, 126.4, 125.9, 123.2, 122.7, 112.8, 112.2, 107.4, 86.1, 61.5, 56.6, 32.9, 29.9, 15.2 (21 of 24 carbons found).

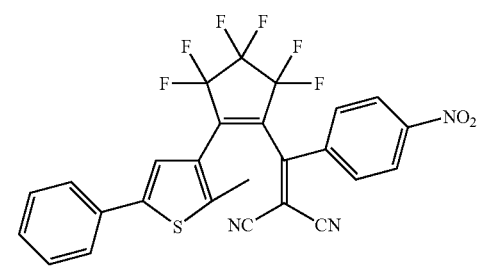

15

(15) Prepared from ketone 8 and purified by column chromatography (SiO$_2$, hexane/ethyl acetate 10:1) as a red solid in 62% yield (34 mg). $^1$H NMR (CDCl$_3$): δ=2.46 (s, 3H), 6.78 (s, 1H), 7.33 (m, 1H), 7.36 (m, 2H), 7.68 (d, J=9.0 Hz, 2H), 8.34 (d, J=9.0 Hz, 2H); $^{13}$C NMR (CDCl$_3$): δ=15.2, 66.1, 92.4, 111.0, 111.2, 122.0, 123.3, 124.2, 124.8, 125.9, 128.9, 129.4, 130.2, 132.4, 137.8, 143.8, 144.3, 150.3, 159.0; $^{19}$F NMR (CDCl$_3$): δ=−108.82, −113.64, −134.56; MS (CI): 546 (M$^+$); Anal Calcd. C, 57.25; H, 2.40; N, 7.70. Found: C, 57.21; H, 2.60; N, 7.50.

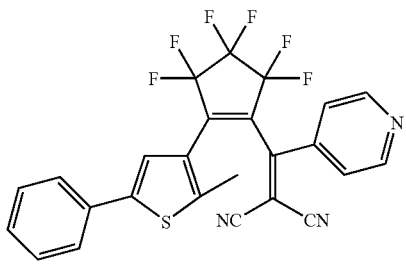

16

(16) A solution of ketone 9 (0.1 mmol) and malonodinitrile (16.5 mg, 0.25 mmol) in anhydrous dichloroethane (5 mL) was cooled in an ice bath to 0° C. under nitrogen atmosphere and treated drop-wise with TiCl$_4$ (0.1 ml, 0.91 mmol). After stirring for 5 min, pyridine (0.2 mL) was carefully added over a 20 min period. The purple reaction mixture was allowed to warm to room temperature and subsequently heated at reflux for 60 min. After cooling to room temperature, the solvents were evaporated under reduced pressure. The solid brown residue was dissolved in H$_2$O (10 mL) and the solution was extracted with chloroform (3×20 mL). The combined organic layers were dried over MgSO$_4$, filtered and concentrated under reduced pressure. Purification by column chromatography (SiO$_2$, hexanes/ethyl acetate 5:2) afforded 16 in 83% yield (42 mg). $^1$H NMR (CDCl$_3$): δ=2.43 (s, 3H), 6.78 (s, 1H), 7.32-7.38 (m, 7H), 8.86 (br s, 2H); $^{13}$C NMR (CDCl$_3$): δ=15.2, 92.7, 111.0, 111.2, 122.0, 126.0, 128.8, 129.4, 132.5, 139.6, 143.6, 144.2, 151.3, 159.0; $^{19}$F NMR (CDCl$_3$): δ=−108.80, −113.59, −134.62; MS (CI): 502 (M$^+$); EA: Anal Calcd. C, 59.88; H, 2.61; N, 8.38. Found: C, 59.71; H, 2.86; N, 8.13.

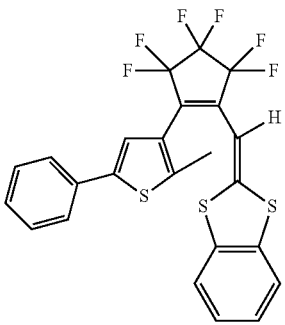

17

Synthesis of Compound 17

In a 10 mL flask, a suspension of (22.5 mg, 0.06 mmol) of aldehyde 3 and 1,3-benzodithiolyl-triphenylphosphonium tetrafluoroborate (30 mg, 0.06 mmol) in CH$_2$Cl$_2$ (0.3 mL) was treated with aqueous NaOH (0.3 mL of 50% w/w). The mixture was stirred at room temperature for 3 h and then extracted with CH$_2$Cl$_2$ (3×10 mL). The organic extracts were washed with water (3×5 mL) and sat. NaCl (1×5 mL). After drying over MgSO$_4$ and filtering, the solvent was removed under reduced pressure and the residue purified by column chromatography (SiO$_2$, hexanes/ethyl acetate 10:1) on a short silica plug (Ø2.5 cm×5 cm). The product was isolated as a yellow solid in 72% yield (22.0 mg). M.p. 49-54° C.; $^1$H NMR (CDCl$_3$): δ=2.24 (s, 3H), 6.23 (s, 1H), 7.12-7.18 (m, 3H), 7.29-7.34 (m, 3H), 7.41 (m, 2H), 7.60 (m, 2H); MS (CI): 513 (M$^+$).

Scheme 11

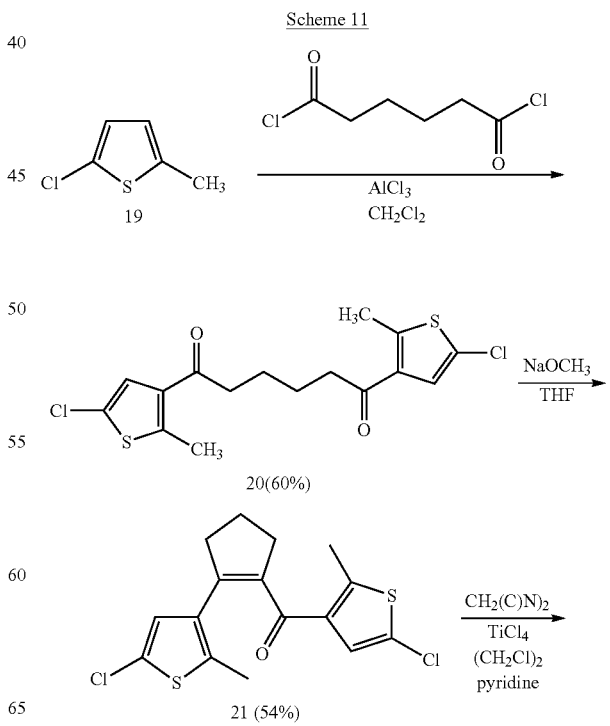

Scheme 10

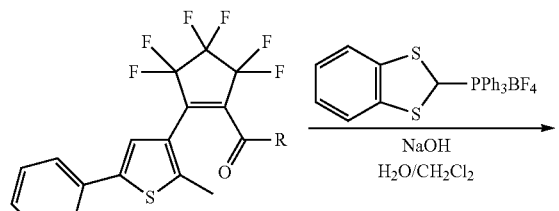

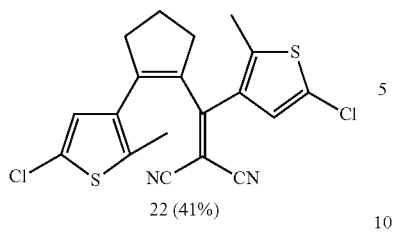

22 (41%)

Synthesis of Diketone 20

A solution of 2-chloro-5-methylthiophene 19 (4.19 g, 31.1 mmol) and adipoyl chloride (2.3 mL, 15.8 mmol) in anhydrous $CH_2Cl_2$ (70 mL) was cooled to 0° C. under nitrogen atmosphere using an ice bath. The solution was treated with portions of $AlCl_3$ (5.30 g, 39.7 mmol). The cooling bath was removed and the solution was allowed to warm at room temperature and was stirred overnight under nitrogen atmosphere. The mixture was poured on an ice (100 g) and aqueous HCl (10 mL) mixture and stirred 1 h. The aqueous layer was separated and extracted with $CH_2Cl_2$ (3×40 mL). The combined organic layers were washed with $NaHCO_3$ (3×100 mL), then brine (100 mL), dried with $MgSO_4$, filtered and evaporated to dryness under reduced pressure. Purification by recrystallization from hexanes afforded 3.60 g of 20 as a colourless solid. (60%). $^1$H NMR ($CDCl_3$): δ=7.16 (s, 2H), 2.80 (m, 4H), 2.65 (s, 6H), 1.74 (m, 4H); $^{13}$C NMR ($CDCl_3$): δ=195.3, 147.8, 135.2, 127.0, 125.5, 41.7, 23.7, 16.2.

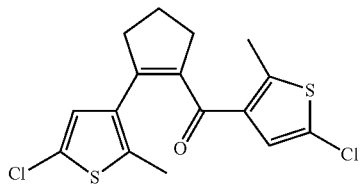

21

Synthesis of Ketone 21

A solution of diketone 20 (1.50 g, 4.0 mmol) in anhydrous THF (150 mL) under nitrogen atmosphere was treated with sodium methoxide (1.10 g, 20 mmol). The solution was heated to reflux for 12 h while kept in the dark and under nitrogen atmosphere. The mixture was allowed to cool to room temperature and treated with aqueous $NH_4Cl$ (150 mL) and stirred for 15 min. The aqueous layer was removed and extracted with diethyl ether (3×20 mL). The combined organic layers were washed with brine (20 mL), dried with $MgSO_4$, filtered and evaporated to dryness under reduced pressure. Purification by column chromatography through silica (1:19 EtOAc:hexanes) afforded a pale yellow oil that was crystallized from $Et_2O$ (777 mg, 54%). $^1$H NMR ($CDCl_3$): δ=6.60 (s, 1H), 6.51 (s, 1H), 2.86 (t, J=7.5 Hz, 2H), 2.78 (t, J=7.5 Hz, 2H), 2.54 (s, 3H), 2.12 (s, 3H), 2.03 (q, J=7.5 Hz, 2H); $^{13}$C NMR ($CDCl_3$): δ=190.5, 145.7, 145.2, 141.4, 136.0, 135.1, 133.6, 128.1, 126.5, 126.3, 124.6, 40.0, 35.3, 22.6, 15.2, 14.3.

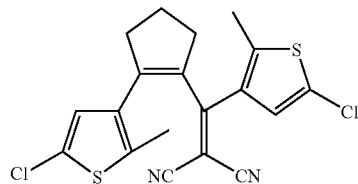

22

Synthesis of Compound 22

A solution of ketone 21 (65 mg, 0.18 mmol) and malonodinitrile (30 mg, 0.45 mmol) in anhydrous dichloroethane (10 mL) under nitrogen atmosphere was cooled to 0° C. using an ice bath. The solution was treated drop-wise with $TiCl_4$ (0.18 mL, 1.6 mmol). After stirring for 5 min, pyridine (0.35 mL) was carefully added over 20 min. The reaction mixture was allowed to warm at room temperature and subsequently heated to reflux for 7 min during which time a white precipitate was formed. After cooling at room temperature, the solvent was evaporated under reduced pressure. The remaining solid was dissolved in 15% aqueous HCl (20 mL) and $CHCl_3$ (10 mL) was added. The water layer was separated and extracted with chloroform (3×10 mL). The combined organic layers were dried over $MgSO_4$, filtered and concentrated under reduced pressure. Purification by column chromatography through silica (1:19 EtOAc:hexanes) afforded 30 mg (41%) of 22 as a yellow oil. $^1$H NMR ($CDCl_3$): δ=6.54 (s, 1H), 6.25 (s, 1H), 2.97 (t, J=7.4 Hz, 2H), 2.77 (t, J=7.4 Hz, 2H), 2.33 (s, 3H), 2.20 (s, 3H), 2.12 (q, J=7.4 Hz, 2H); $^{13}$C NMR ($CDCl_3$) δ=165.3, 153.2, 142.3, 137.8, 135.3, 133.0, 132.6, 127.9, 126.7, 126.4, 126.0, 113.7, 113.2, 40.0, 36.8, 24.0, 15.5, 14.4.

Scheme 12

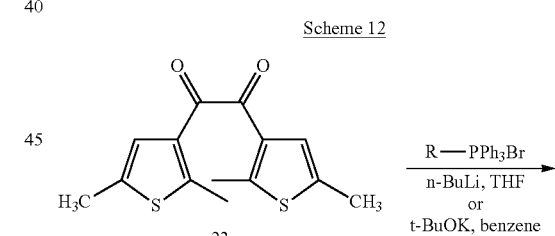

23

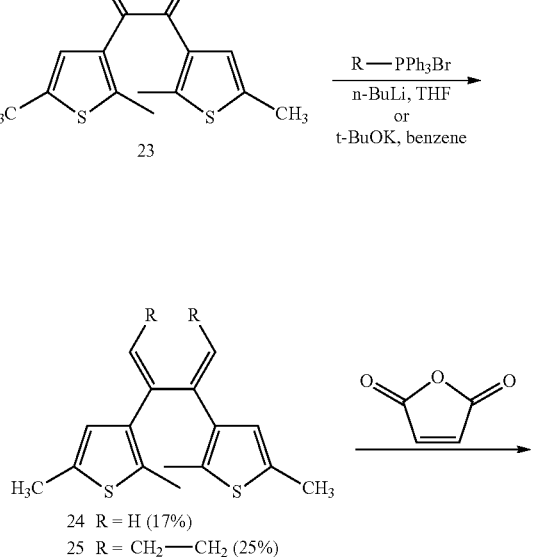

24 R = H (17%)
25 R = $CH_2$—$CH_2$ (25%)

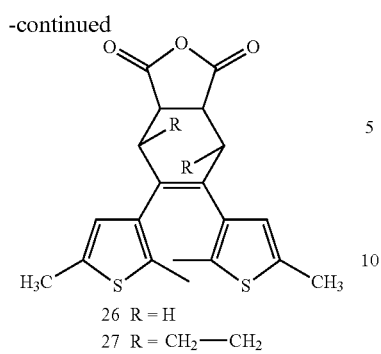

26 R = H
27 R = CH₂—CH₂

Synthesis of 2,3-bis(2,5-dimethyl-3-thienyl)-1,3-butadiene (24)

n-Butyllithium (0.64 ml of a 2.5 M solution in hexanes, 1.6 mmol) was added drop-wise to a cooled (0° C.) suspension of methyltriphenylphosphonium bromide (568 mg, 1.6 mmol) in THF (50 mL). After the addition was completed, the ice bath was removed and the reaction mixture was allowed to slowly warm to room temperature, at which point it was stirred for 45 min. The resulting yellow solution was cooled to −78° C. and treated drop-wise with a solution of 1,2-bis(2,5-dimethyl-3-thienyl)ethanedione 23 (89 mg, 0.32 mmol) in THF (10 mL). The reaction mixture was stirred at −78° C. for 30 min, the dry ice/acetone bath was removed and the reaction was allowed to warm to room temperature. After stirring overnight, the reaction was quenched by the addition of water (50 mL) and extracted with Et₂O (3×50 mL). The organic extracts were combined, washed with brine, dried over MgSO₄ and filtered. The solvent was removed under reduced pressure and the residue was purified by column chromatography through silica (1:9 EtOAc:hexanes) to yield 15 mg (17%) of diene 24 as a white solid. Mp=43-44° C.; ¹H NMR (CDCl₃); δ=6.52 (s, 2H), 5.13 (d, J=3.4 Hz, 2H), 5.09 (d, J=3.4 Hz, 2H), 2.40 (s, 6H), 2.31 (s, 6H); ¹³C NMR (CDCl₃): δ=144.5, 137.7, 135.1, 133.0, 127.9, 118.5, 15.4, 14.1; MS (EI): m/z=274 (M⁺).

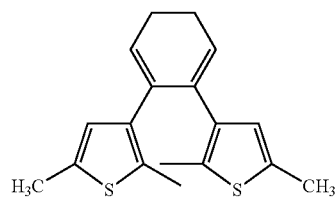

Synthesis of 3,4-bis(2,5-dimethyl-3-thienyl)cyclohexadiene (25)

Potassium t-butoxide (163 mg, 1.45 mmol) was added to a suspension of 1,4-butanebis(triphenylphosphonium)dibromide (537 mg, 0.725 mmol) in benzene (50 mL). The reaction was stirred for 45 min at room temperature. The resulting orange solution was heated to reflux and treated drop-wise with a solution of 1,2-bis(2,5-dimethyl-3-thienyl)ethanedione 23 (202 mg, 0.72 mmol) in benzene (25 mL). The reaction mixture was stirred at reflux for 20 min, at which point the heating mantle was removed and the reaction was allowed to cool to room temperature. The reaction was quenched by the addition of water (50 mL) and extracted with Et₂O (3×50 mL). The organic extracts were combined, washed with brine, dried over MgSO₄ and filtered. The solvent was removed under reduced pressure and the residue was purified by column chromatography through silica (1:9 EtOAc:hexanes) to yield 55 mg (25%) of 25 as a white solid. Mp=55-57° C. ¹H NMR (CDCl₃): δ=6.13 (s, 2H), 5.88 (m, 2H), 2.26 (m, 10H), 2.14 (s, 6H); ¹³C NMR (CDCl₃) δ=137.8, 134.4, 133.9, 131.6, 127.4, 126.7, 22.7, 15.1, 14.0. MS (EI): m/z=300 (M⁺).

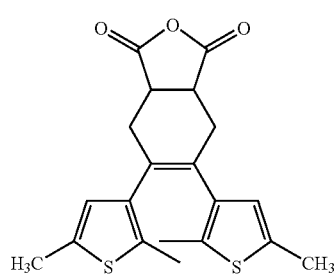

Synthesis of Cyclohexene 26

A solid mixture of 2,3-bis(2,5-dimethyl-3-thienyl)-1,3-butadiene 24 (6.8 mg, 0.03 mmol) and maleic anhydride (4.9 mg, 0.05 mmol) was heated to 70° C. using an oil bath. Upon the complete melting of both solids, a pale pink solid formed. The cyclohexene product (26) was purified by column chromatography through silica (1:4 EtOAc:hexanes) as a white solid. ¹H NMR (CDCl₃): δ=6.32 (s, 2H), 3.53 (d, J=2.4 Hz, 2H), 2.96 (d, J=15.1 Hz, 2H), 2.65 (dd, J=15.1, 2.4 Hz, 2H), 2.33 (s, 6H), 1.73 (s, 6H).

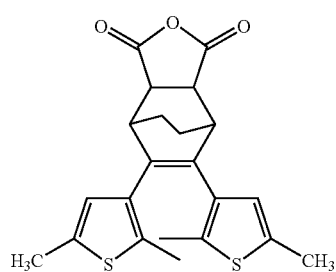

Synthesis of Bicyclic Product 27—Procedure 1

3,4-Bis(2,5-dimethyl-3-thienyl)cyclohexadiene 25 (5 mg) and maleic anhydride (5 mg) were mixed in a 10 mL round bottom flask. The mixture turned from colorless to yellow within the first few seconds. After standing for 1 h at room temperature, product 27 was purified by column chromatography through silica (1:4 EtOAc:hexanes) as a white solid. The efficiency of the reaction was greatly improved when melting both components by heating to 70° C. in an oil bath. ¹H NMR (CDCl₃): δ=6.45 (s, 2H), 3.43 (m, 2H), 3.26 (m, 2H), 2.35 (s, 6H), 1.65 (s, 6H), 1.54 (m, 4H). MS (EI: m/z=398 (M⁺).

Procedure 2

3,4-Bis(2,5-dimethyl-3-thienyl)cyclohexadiene 25 (1 mg) and maleic anhydride (1 mg) were dissolved in acetone-d₆ (1 mL) in an NMR tube and heated to 65° C. in a water bath. The reaction went to completion after 7 days and no side products were observed by $^1$H NMR spectroscopy. NMR (acetone-$d_6$): δ=6.55 (s, 2H), 3.54 (m, 2H), 3.35 (m, 2H), 2.35 (s, 6H), 1.89 (dm, J=7.4 Hz, 2H), 1.65 (dm, J=7.4 Hz, 2H), 1.65 (s, 6H).

Procedure 3

3,4-Bis(2,5-dimethyl-3-thienyl)cyclohexadiene 25 (20 mg, 6.8×10$^{-5}$ mol) and maleic anhydride (6.5 mg, 6.8×10$^{-5}$ mol) were dissolved in acetone-$d_6$ (0.75 mL) in an NMR tube and heated at 65° C. in a water bath. The reaction went to completion after 5 days and no side products were observed by $^1$H NMR spectroscopy. Thin layer chromatography and $^{13}$C NMR spectroscopy showed the presence of trace amount of impurities. The product was purified by column chromatography through silica (1:4 EtOAc:hexanes). Mp=>185° C. (decomposition); $^1$H NMR (acetone-$d_6$): δ=6.55 (s, 2H), 3.54 (m, 2H), 3.35 (m, 2H), 2.35 (s, 6H), 1.89 (dm, J=7.4 Hz, 2H), 1.65 (m, 2H), 1.65 (s, 6H); $^{13}$C NMR (acetone-$d_6$): δ=175.2, 137.8, 137.3, 136.9, 133.9, 127.2, 46.8, 40.7, 25.2, 15.9, 14.8; MS (EI): m/z=398 (M$^+$).

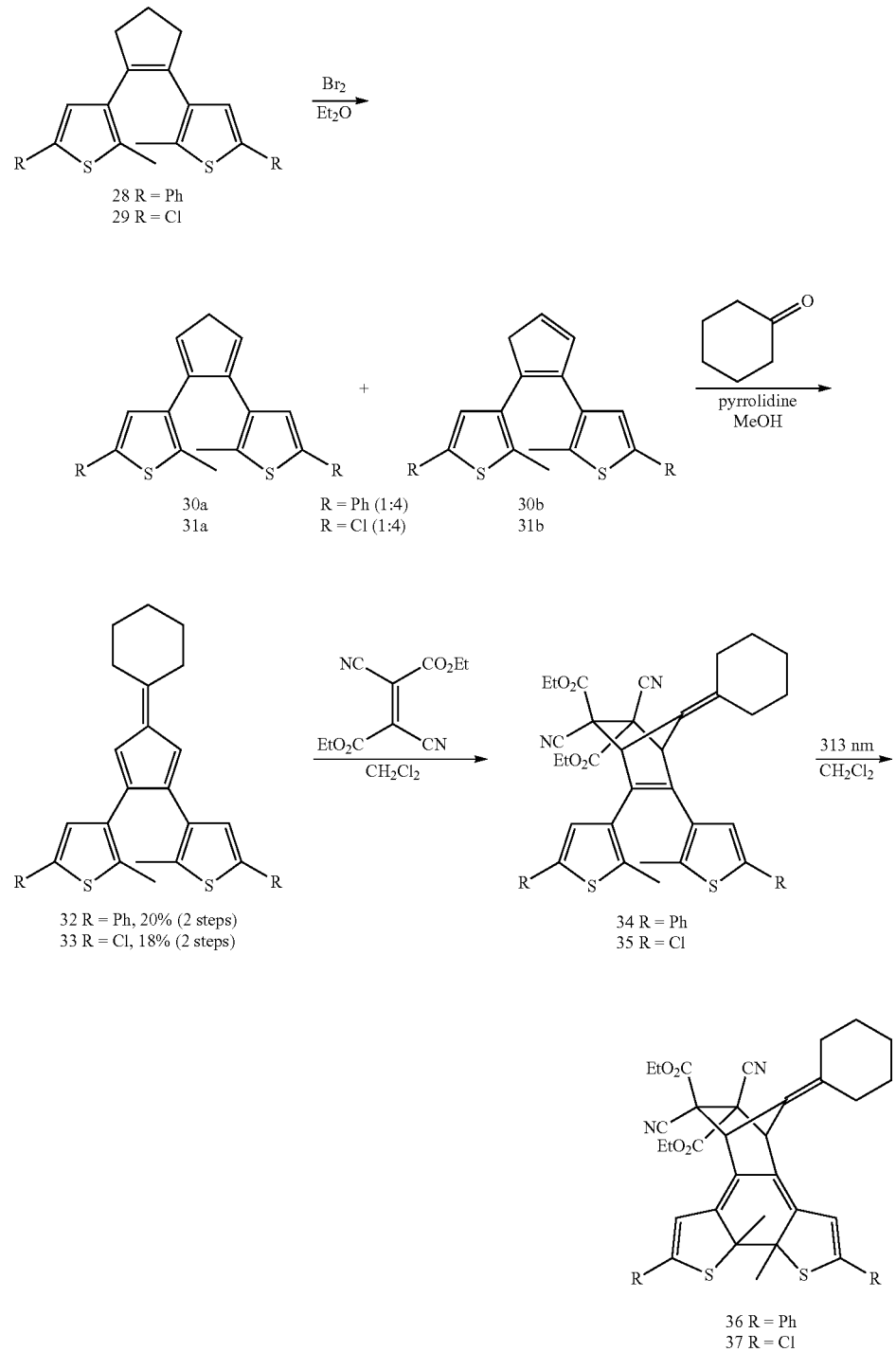

Synthesis of Cyclopentadiene Isomers 30a and 30b

A solution of 1,2-bis(5'-phenyl-2'-methylthieny-3'-yl)cyclopentene (28) (280 mg, 0.73 mmol) in anhydrous Et$_2$O (50 mL) was cooled to −40° C. under nitrogen atmosphere using an acetone/dry ice bath. The solution was kept in the dark while it was treated with bromine (36 μL 0.73 mmol) in one portion using a syringe. The cooling bath was removed, the reaction was allowed to warm to room temperature and was stirred for 1 h. The reaction was quenched with water (10 mL) and stirred for 10 min. The aqueous layer was separated and extracted with Et$_2$O (3×50 mL). The combined organic layers were washed with water (10 mL), then brine (10 mL), dried with Na$_2$SO$_4$, filtered and evaporated to dryness under reduced pressure. Purification by column chromatography through silica (18:1 hexanes:EtOAc containing 1% Et$_3$N) afforded a colorless oil containing the isomers 30a and 30b in a 1:4 ratio.

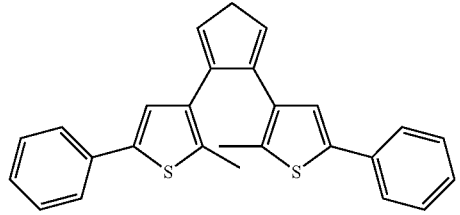

30a (30a) $^1$H NMR (CDCl$_3$): δ=7.42 (d, J=7.7 Hz, 4H), 7.29 (t, J=7.7 Hz, 4H), 7.21 (t, J=7.7 Hz, 2H), 6.87 (s, 2H), 6.48 (t, J=1.5 Hz, 2H), 3.28 (t, J=1.5 Hz, 2H), 2.27 (s, 6H).

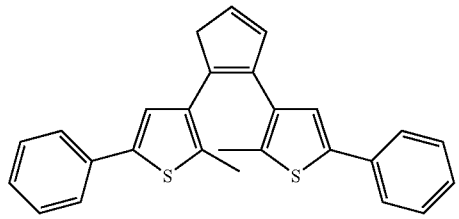

30b (30b) $^1$H NMR (CDCl$_3$): δ=7.50 (d, J=7.6 Hz, 4H), 7.33 (t, J=7.6 Hz, 4H), 7.22 (t, J=7.6 Hz, 2H), 7.09 (s, 1H), 7.08 (s, 1H), 6.71 (dt, J=5.5, 1.5 Hz, 1H), 6.53 (dt, J=5.5, 1.5 Hz, 1H), 3.50 (t, J=1.5 Hz, 2H), 2.12 (s, 3H), 2.03 (s, 3H).

Synthesis of Cyclopentadiene Isomers 31a and 31b

A solution of 1,2-bis(5'-chloro-2'-methylthieny-3'-yl)cyclopentene 29 (203 mg, 0.61 mmol) in anhydrous Et$_2$O (25 mL) was cooled to −40° C. under nitrogen atmosphere using an acetone/dry ice bath. The solution was kept in the dark while it was treated with bromine (31 μL, 0.61 mmol) in one portion using a syringe. The cooling bath was removed, the reaction was allowed to warm to room temperature and was stirred for 1 h. The reaction was quenched with water (10 mL) and stirred for 10 min. The aqueous layer was separated and extracted with Et$_2$O (3×50 mL). The combined organic layers were washed with water (10 mL) and brine (10 mL), dried with MgSO$_4$, filtered and evaporated to dryness under reduced pressure. Purification by column chromatography through silica (19:1 hexanes:EtOAc containing 1% Et$_3$N) afforded 94 mg (47%) of a colorless oil containing the isomers 31a and 31b in a 1:4 ratio.

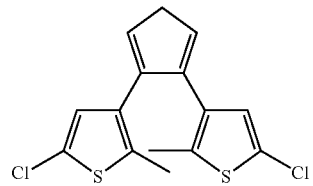

31a (31a) $^1$H NMR (CDCl$_3$): δ=6.41 (s, 2H), 6.38 (t, J=1.8 Hz, 2H), 3.22 (t, J=1.8 Hz, 2H), 2.16 (s, 6H). $^1$H NMR (acetone-D$_6$) δ 6.50 (t, J=1.8 Hz, 2H), 6.48 (s, 2H), 3.28 (t, J=1.8 Hz, 2H), 2.20 (s, 6H).

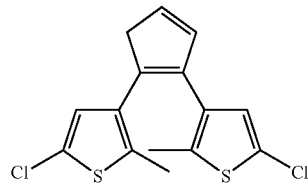

31b (31b) $^1$H NMR (CDCl$_3$): δ=6.63 (s, 1H), 6.62 (s, 1H), 6.57 (dt, J=1.5, 5.2 Hz, 1H), 6.48 (dt, J=1.5, 5.2 Hz, 1H), 3.36 (t, J=1.5 Hz, 2H), 2.02 (s, 3H), 1.92 (s, 3H); $^1$H NMR (acetone-D$_6$): δ=6.84 (s, 1H), 6.73 (s, 1H), 6.65 (dt, J=1.5, 5.4 Hz, 1H), 6.55 (dt, J=1.5, 5.4 Hz, 1H), 3.47 (t, J=1.5 Hz, 2H), 2.06 (s, 3H), 1.94 (s, 3H): $^{13}$C NMR (acetone-D$_6$): δ=139.0, 138.6, 137.1, 136.2, 136.1, 136.0, 135.1, 134.7, 129.8, 129.3, 126.7, 126.4, 47.4, 15.2, 15.1.

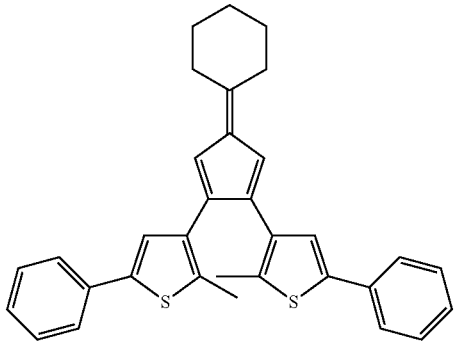

32

One-pot synthesis of 2,3-bis(2'-phenyl-5'-methylthieny-3'-yl)-6,6-pentamethylenefulvene (32). A solution of 1,2-bis(5'-phenyl-2'-methylthieny-3'-yl)cyclopentene (28) (1.00 g, 2.40 mmol) in anhydrous Et$_2$O (100 mL) was cooled to −40° C. under nitrogen atmosphere using an acetone/dry ice bath. The solution was kept in the dark while it was treated with bromine (125 pt, 2.4 mmol) in one portion using a syringe. The cooling bath was removed, the reaction was allowed to warm to room temperature and was stirred in the dark under nitrogen atmosphere. The reaction was monitored by TLC (hexanes). After approximately 1 h all starting materials had been consumed and water (10 mL) was added to quench any unreacted bromine. The reaction was stirred for 10 min when the aqueous layer was separated and extracted with Et$_2$O (3×20 mL). The combined organic extracts were washed with water (10 mL) and brine (10 mL), dried with Na$_2$SO$_4$, filtered and evaporated to dryness under reduced pressure. The crude product was dissolved in methanol (50 mL) and was deoxygenated by bubbling nitrogen gas through it for 30 min. It was then treated with deoxygenated cyclohexanone (0.50 mL, 4.8 mmol) and deoxygenated pyrrolidine (410 µL, 4.8 mmol). The reaction was stirred at room temperature for 12 h in the dark. The methanol was evaporated in vacuo to yield a brown solid. The crude mixture was dissolved in Et$_2$O (100 mL), washed with water (20 mL) and brine (20 mL), dried over Na$_2$SO$_4$ and evaporated under reduced pressure to yield a brown solid. Purification by column chromatography using silica (hexanes) afforded 242 mg (20%) of 32 as a yellow solid. Mp. 163° C.; $^1$H NMR (CD$_2$Cl$_2$): δ=7.46 (d, J=7.8 Hz, 4H), 7.30 (t, J=7.8 Hz, 4H), 7.20 (t, J=7.8 Hz, 2H) 6.93 (s, 2H), 6.66 (s, 2H), 2.74 (m, 4H), 2.32 (s, 6H), 1.82 (m, 4H), 1.74 (m, 2H); $^{13}$C NMR (CD$_2$Cl$_2$): δ=160.5, 141.9, 140.9, 140.1, 137.4, 137.0, 136.4, 130.6, 128.8, 127.4, 127.2, 121.0, 35.5, 30.8, 28.4, 16.1; MS (CI) m/z=491 (M+1), 493 (M+3); MS (EI) m/z=492 (M+2); EA (calc.) C, 80.77; H, 6.16; (exp.) C, 80.39; H, 6.35.

reduced pressure to yield a brown solid. Purification by column chromatography using silica (hexanes) afforded 222 mg (18%) of 33 as a yellow solid. Mp. 144-146° C.; $^1$H NMR (CD$_2$Cl$_2$): δ=6.57 (s, 2H), 6.47 (s, 2H), 2.70 (m, 4H), 2.21 (s, 6H), 1.78 (m, 4H), 1.72 (m, 2H); $^{13}$C NMR (CD$_2$Cl$_2$): δ=159.6, 138.4, 137.5, 133.5, 133.4, 127.6, 124.2, 119.4, 33.3, 28.6, 26.1, 13.6; MS (EI) m/z=406 (M$^+$); EA (calc.) C, 61.91; H, 4.95; (exp.) C, 61.81; H, 5.08.

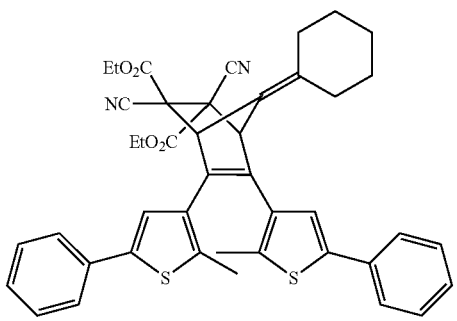

34

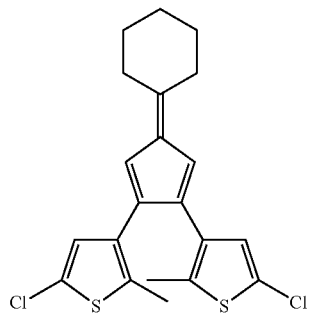

33

One-pot synthesis of 2,3-bis(2'-chloro-5'-methylthieny-3'-yl)-6,6-pentamethylenefulvene (33)

A solution of 1,2-bis(5'-chloro-2'-methylthieny-3'-yl)cyclopentene (29) (1.00 g, 3.04 mmol) in anhydrous Et$_2$O (75 ml) was cooled to −40° C. under nitrogen atmosphere using an acetone/dry ice bath. The solution was kept in the dark while it was treated with bromine (160 µL, 3.0 mmol) in one portion using a syringe. The cooling bath was removed, the reaction was allowed to warm to room temperature and was stirred in the dark under nitrogen atmosphere. The reaction was monitored by TLC (hexanes). After approximately 2 h, all starting materials had been consumed and water (10 mL) was added to quench any unreacted bromine. The reaction was stirred for 10 min when the aqueous layer was separated and extracted with Et$_2$O (3×20 mL). The combined organic extracts were washed with water (10 mL), NaHCO$_3$ saturated aqueous solution (10 mL), and brine (10 mL), dried with MgSO$_4$, filtered and evaporated to dryness under reduced pressure. The crude product was dissolved in methanol (50 mL) and was deoxygenated by bubbling nitrogen gas through it for 30 min. It was then treated with deoxygenated cyclohexanone (1.56 mL, 15.2 mmol) and deoxygenated pyrrolidine (1.27 mL, 15.2 mmol). The reaction was stirred at room temperature for 14 h in the dark. The methanol was evaporated in vacuo to yield a brown solid. The crude mixture was dissolved in Et$_2$O (100 mL), washed with water (20 mL) and brine (20 mL), dried over MgSO$_4$ and evaporated under Synthesis of Bicyclic Compound 34

A solution of fulvene 32 (5.0 mg, 0.01 mmol) in CD$_2$Cl$_2$ (0.75 mL) was treated with diethyldicyanofumerate (9.4 mg, 0.05 mmol) in one portion in an NMR tube. The reaction was monitored by $^1$H NMR spectroscopy and reached equilibrium within 20 minutes when 45% of product was obtained. The equilibrium constant (K$_{eq}$) was calculated to be 16 M$^{-1}$. $^1$H NMR (CD$_2$Cl$_2$): δ=7.56 (m, 4H), 7.50 (s, 1H), 7.39 (m, 6H), 7.16 (m, 1H), 4.40-4.00 (m, 6H), 2.7-2.6 (m, 2H), 2.3-2.0 (m, 2H), 1.97 (s, 3H), 1.92 (s, 3H), 1.63 (m, 6H), 1.16 (m, 6H).

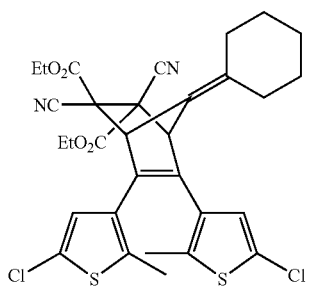

35

Synthesis of Bicyclic Compound 35

A solution of the fulvene 33 (5.5 mg, 0.01 mmol) in CD$_2$Cl$_2$ (0.75 mL) at room temperature was treated with diethyldicyanofumerate (11 mg, 0.05 mmol) in one portion in an NMR tube. The reaction was monitored by $^1$H NMR spectroscopy and reached equilibrium within 20 minutes when 43% of product was obtained. The equilibrium constant (K$_{eq}$) was calculated to be 13 M$^{-1}$. $^1$H NMR (CD$_2$Cl$_2$): δ=7.02 (s, 1H), 6.77 (s, 1H), 4.30 (s, 2H), 4.3-4.2 (m, 2H), 4.1-4.0 (m, 2H), 2.5-2.0 (m, 4H), 1.84 (s, 3H), 1.81 (s, 3H), 1.7-1.4 (m, 6H), 1.42 (t, 3H), 1.23 (t, 3H).

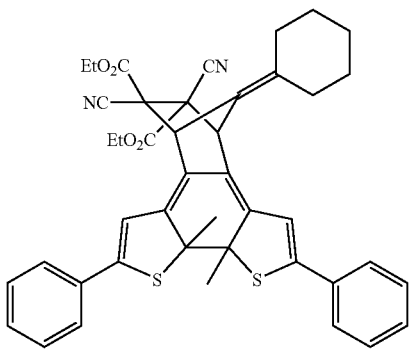

Synthesis of Ring-Closed Compound 36

A solution of fulvene 32 (50 mg, 0.1 mmol) in CH₂Cl₂ (15 mL) was treated with diethyldicyanofumarate (68 mg, 0.3 mmol). The solution was kept in the dark while it was stirred for 15 min. The solution was then irradiated with 313-nm light for 15 min. Further irradiation resulted in the formation of a significant amount of an uncharacterized side product. The solution was evaporated under vacuum and in the dark to yield a red/purple solid. Purification by column chromatography in the dark using silica (hexanes:EtOAc 18:1) afforded 36 as a mixture of two stereoisomers which were not separated. In order to avoid ring-opening of 36, the compound must be kept in absolute darkness. Stereoisomer 1 (major): $^1$H NMR (CD₂Cl₂): δ=7.54 (m, 4H)*, 7.39 (m, 6H)*, 6.57 (s, 1H), 6.51 (s, 1H), 4.40-4.20 (m, 6H)*, 2.5-2.1 (m; 6H)*, 2.05 (s, 3H)*, 1.98 (s, 3H)*, 1.7-1.5 (m, 4H), 1.39 (m, 6H)*. Stereoisomer 2 (minor): $^1$H NMR (CD₂Cl₂): δ=7.54 (m, 4H)*, 7.39 (m, 6H)*, 6.55 (s, 1H), 6.52 (s, 1H), 4.40-4.20 (m, 6H)*, 2.5-2.1 (m, 6H)*, 2.05 (s, 3H)*, 1.98 (s, 3H)*, 1.7-1.5 (m, 4H), 1.39 (m, 6H)*. (*Observed as overlapping peaks of stereoisomers.)

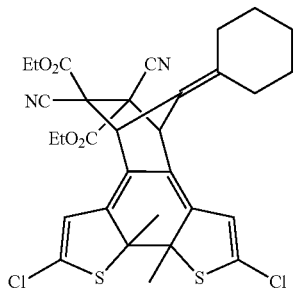

Synthesis of Ring-Closed Compound 37

A solution of fulvene 33 (56 mg, 0.1 mmol) in CH₂Cl₂ (7.5 mL) was treated with diethyldicyanofumarate (116 mg, 0.5 mmol). The solution was kept in the dark while it was stirred for 1 h. The solution was then irradiated with 313-nm light for 8 minutes. Further irradiation resulted in the formation of a significant amount of an uncharacterized side product. The solution was evaporated under vacuum and in the dark to yield a yellow/orange solid. Purification by column chromatography in the dark using silica (hexanes:EtOAc 19:1) afforded 37 as a mixture of two stereoisomers. Recrystallization with hexanes afforded a solid enriched with the major stereoisomer and a solute enriched with the minor stereoisomer. In order to avoid ring-opening of 37, the compound must be kept in absolute darkness. Stereoisomer 1 (major): NMR (CD₂Cl₂): δ=6.10 (s, 1H), 6.06 (s, 1H), 4.40-4.20 (m, 4H)*, 4.17 (s, 1H), 4.12 (s, 1H)*, 2.40-2.25 (m, 4H)*, 2.15-2.10 (m, 2H)*, 2.02 (s, 3H)*, 1.94 (s, 3H)*, 1.7-1.5 (m, 4H)*, 1.39 (m, 6H)*. Stereoisomer 2 (minor): $^1$H NMR (CD₂Cl₂): S=6.08 (s, 1H), 6.05 (s, 1H), 4.40-4.20 (m, 4H)*, 4.12 (s, 1H)*, 4.06 (s, 1H), 2.40-2.25 (m, 4H)*, 2.15-2.10 (m, 2H)*, 2.02 (s, 3H)*, 1.94 (s, 3H)*, 1.7-1.5 (m, 4H)*, 1.39 (m, 6H)*. (*Observed as overlapping peaks of stereoisomers.)

Photocyclization Reactions of Compounds 10-17

Scheme 14 below shows reversible photocyclization of compounds 10-17 at different wavelengths of light, namely 365 nm light for conversion from the ring-open to the ring-closed form, and 490 nm light for conversion from the ring-closed and ring-open form.

Scheme 14

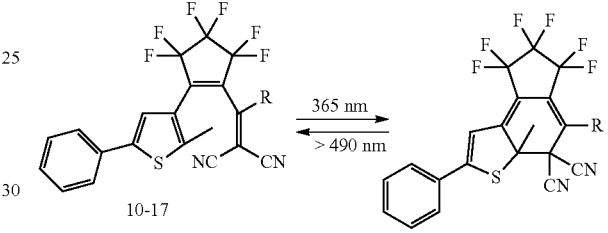

Characterization of Compounds 10-17

Figure 2:
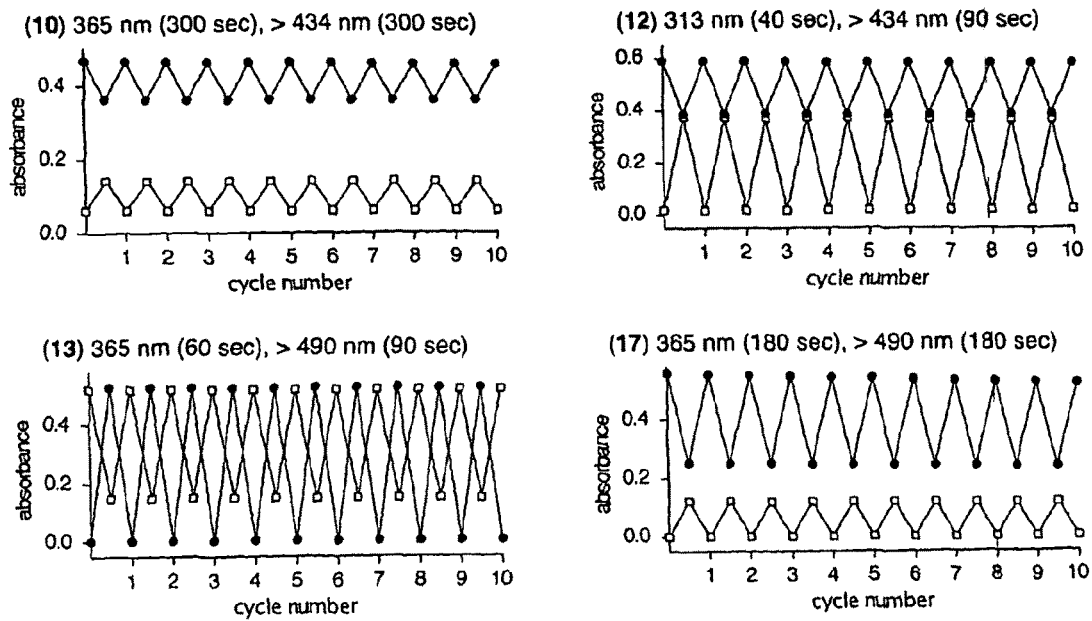
FIG. 2 are graphs showing the modulated absorptions of the ring-open isomers (□) and the ring-closed isomers (●) during alternating UV and VIS irradiations. The irradiation wavelengths and times for each compound are provided in the figure.

FIG. 1 are graphs showing changes in the UV-VIS absorption spectra of solutions of compounds 10-17 when irradiated with 365-nm light (313 nm for 12). The solvent, concentrations and total irradiation times for each compound are provided in the figure. FIG. 2 are graphs showing the modulated absorptions of the ring-open isomers (□) and the ring-closed isomers (●) during alternating UV and VIS irradiations. The irradiation wavelengths and times for each compound are provided in the figure. One UV and one VIS irradiation occurs in each cycle. The FIGS. 1 and 2 graphs demonstrate that compounds 10-17 are photoactive, i.e. there is a change in the absorption spectra of each compound when they are irradiated and there is little degradation when the compounds are subjected to several ring-closing/ring-opening cycles.

Characterization of Compound 24

Figure 3:
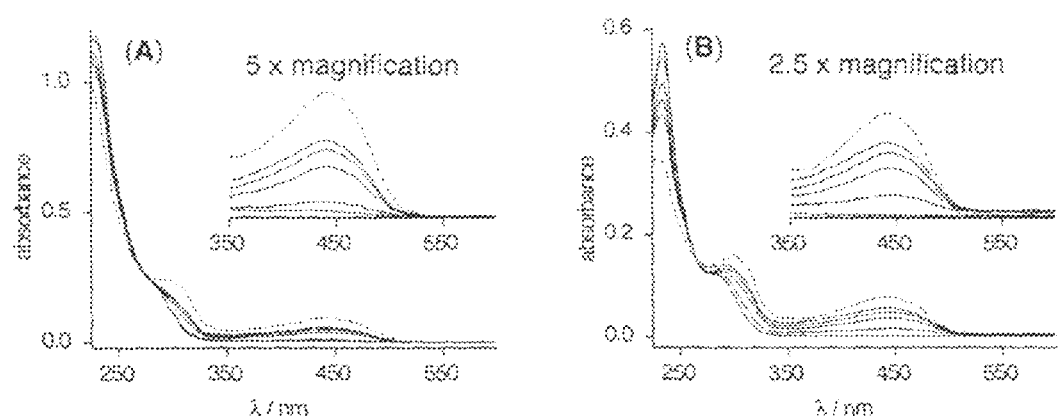
FIG. 3A is a graph showing changes in the UV-VIS absorption spectra when an acetonitrile solution ($2 \times 10^{-5}$ M) of 26 is irradiated with 313-nm light for a total of 45 seconds (solid lines) and 254-nm light for 45 seconds (dashed line).
FIG. 3B is a graph showing changes in the UV-VIS absorption spectra when an acetonitrile solution ($2 \times 10^{-5}$ M) of 27 is irradiated with 313-nm light for a total of 45 seconds (solid lines) and 254-nm light for 45 seconds (dashed line).

FIG. 3A is a graph showing changes in the UV-VIS absorption spectra when an acetonitrile solution (2×10⁻⁵ M) of 26 is irradiated with 313-nm light for a total of 45 seconds (solid lines) and 254-nm light for 45 seconds (dashed line). FIG. 3B is a graph showing changes in the UV-VIS absorption spectra when an acetonitrile solution (2×10⁻⁵ M) of 27 is irradiated with 313-nm light for a total of 45 seconds (solid lines) and 254-nm light for 45 seconds (dashed line). The experimental data shown in FIGS. 3A and 3B confirm that compounds 24 and 25 are photoactive.

Characterization of the photostationary state containing 25 and 27.

A CDCl₃ solution of 25 (1×10⁻³M) was irradiated with 313-nm light for 1-minute periods and $^1$H NMR spectra were obtained after each irradiation. The photostationary state (containing 31% of the ring-closed isomer 27) was obtained after a total of 4 minutes of irradiation.

(27) $^1$H NMR (CDCl$_3$): δ=7.72 (s, 1H), 7.50 (s, 1H), 3.23 (m, 1H), 3.22 (m, 1H), 3.12 (m, 1H), 3.11 (m, 1H), 2.08 (s, 6H), 1.89 (s, 3H), 1.84 (s, 3H), 1.54 (m, 4H).

Figure 4:
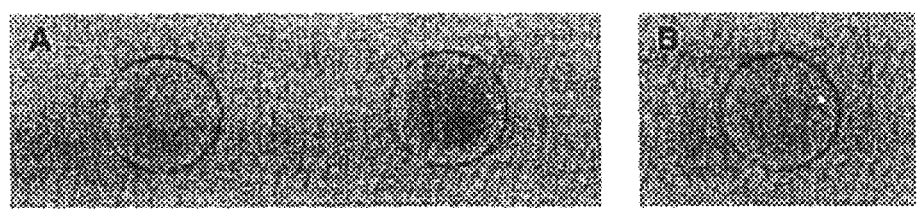
FIG. 4A is a picture showing the color change that occurs when a DMSO solution of diene 25 and excess maleic anhydride are mixed and exposed to 313-nm light (right spot). The left spot is a sample containing only the diene 25 that has been simultaneously irradiated. Cyclohexadiene 25 (1 mg) was added to a saturated solution of maleic anhydride in DMSO (0.5 mL) and a small amount of DMSO was added (~0.5 mL) to dissolve the remaining solid. A solution containing only the cyclohexadiene was also prepared (1 mg in 1 mL). One drop of each solution was deposited on a microscope slide and placed on a heating stage at 35° C. for 30 minutes. After this heating period, the samples were simultaneously irradiated for 30 seconds with 313-nm light. The sample containing maleic anhydride and the cyclohexadiene turned yellow. The other did not. The same behaviour was observed when the solution of maleic anhydride and cyclohexadiene and the control solution were kept at room temperature for 14 hours.
FIG. 4B shows the same sample of diene 25 and maleic anhydride after bleaching with greater than 415-nm light.

FIG. 4A is a picture showing the color change that occurs when a DMSO solution of diene 25 and excess maleic anhydride are mixed and exposed to 313-nm light (right spot). The left spot is a sample containing only the diene 25 that has been simultaneously irradiated. Cyclohexadiene 25 (1 mg) was added to a saturated solution of maleic anhydride in DMSO (0.5 mL) and a small amount of DMSO was added (~0.5 mL) to dissolve the remaining solid. A solution containing only the cyclohexadiene was also prepared (1 mg in 1 mL). One drop of each solution was deposited on a microscope slide and placed on a heating stage at 35° C. for 30 minutes. After this heating period, the samples were simultaneously irradiated for 30 seconds with 313-nm light. The sample containing maleic anhydride and the cyclohexadiene turned yellow. The other did not. The same behaviour was observed when the solution of maleic anhydride and cyclohexadiene and the control solution were kept at room temperature for 14 hours. FIG. 4B shows the same sample of diene 25 and maleic anhydride after bleaching with greater than 415-nm light. These experiments illustrate the gated photochromism, where the thermal Diels-Alder reaction must occur before the compounds can undergo photoinduced ring-closing.

Characterization of Compounds 32-37

Figure 5:
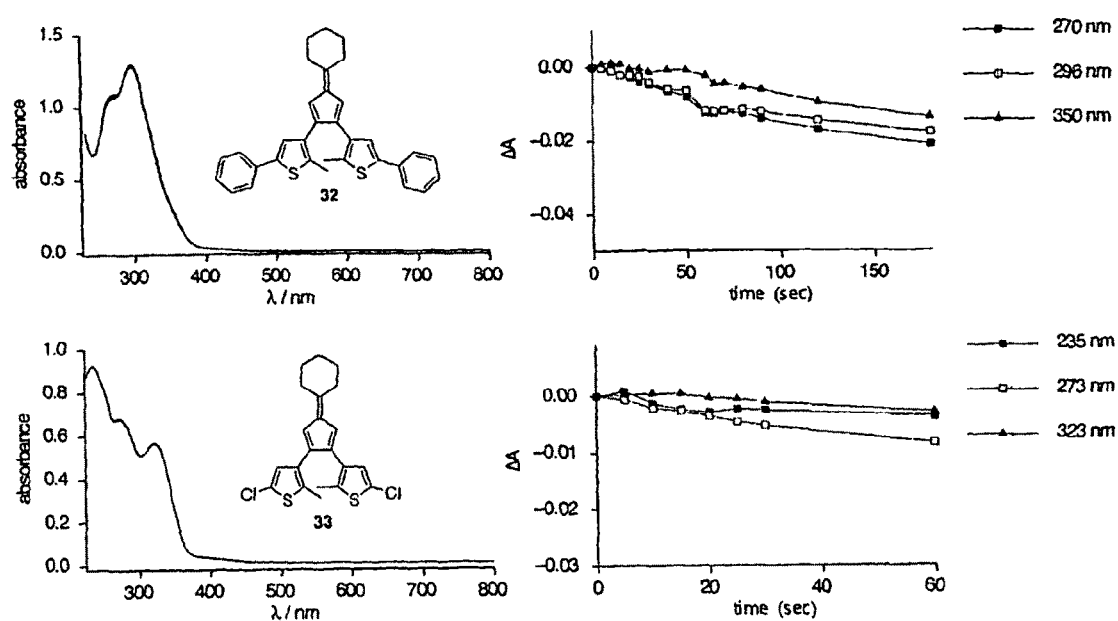
FIG. 5 are graphs showing the insignificant changes in the UV-VIS absorption spectra when $CH_2Cl_2$ solutions of the non-photoactive compounds 32 and 33 are irradiated with UV light. In the case of 32, the light source was changed to >490 nm after 60 seconds.

FIG. 5 are graphs showing insignificant changes in the UV-VIS absorption spectra when CH$_2$Cl$_2$ solutions of compounds 32 and 33 are irradiated with UV light. In the case of 32, the light source was changed to >490 nm after 60 seconds. These graphs demonstrate the photostability of compounds 32 and 33.

Figure 6:
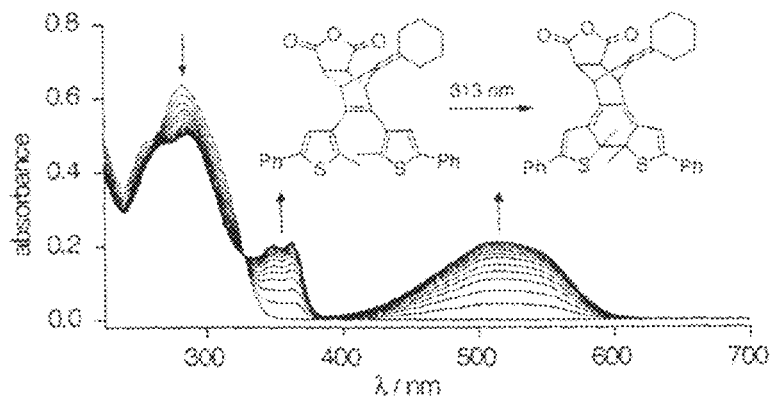
FIG. 6 is a graph showing changes in the UV-VIS absorption spectra when a $CH_2Cl_2$ solution ($2.5 \times 10^{-5}$ M) of the product obtained from the thermal reaction of fulvene 32 and maleic anhydride is irradiated with 313-nm light for a total of 60 seconds.

FIG. 6 is a graph showing changes in the UV-VIS absorption spectra when a CH$_2$Cl$_2$ solution (2.5×10$^{-5}$ M) of the product obtained from the thermal reaction of fulvene 32 and maleic anhydride when the product is irradiated with 313-nm light for a total of 60 seconds. These data confirm that compound 34 is photoactive.

Figure 7:
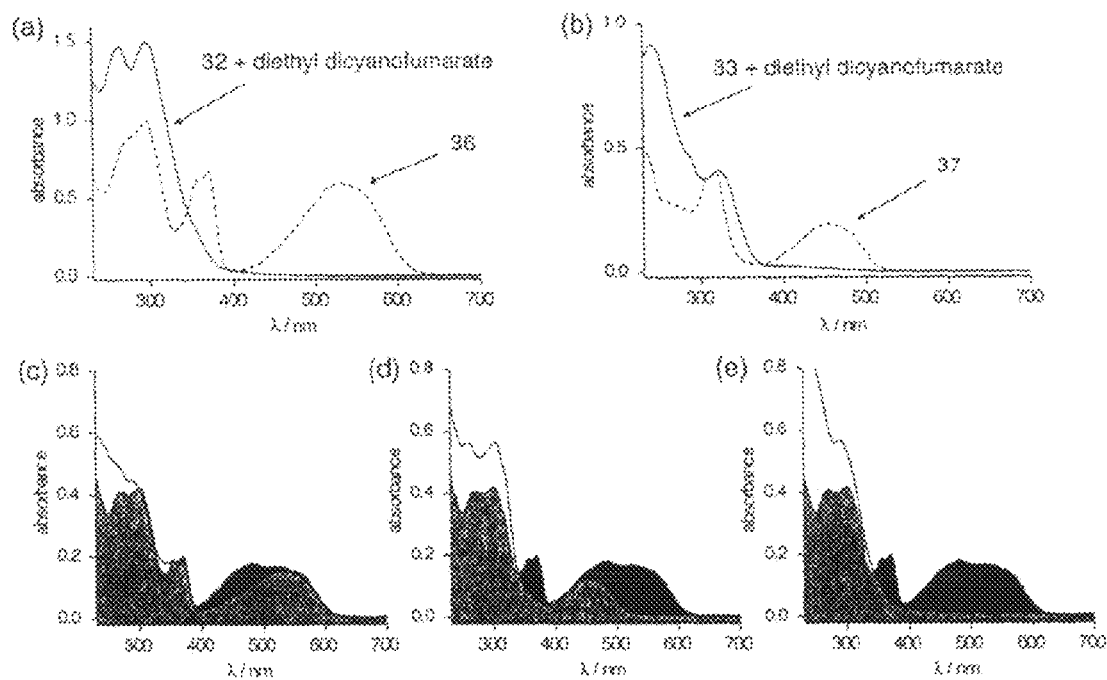
FIG. 7 are UV-VIS absorption spectra: (a) UV-VIS absorption spectra of a $CH_2Cl_2$ solution ($3.4 \times 10^{-5}$ M) of the ring-closed isomer 36 and a 1:1 mixture of 32 and diethyl dicyanofumarate obtained after the irradiation of 36 with light of wavelengths greater than 490 nm. (b) UV-VIS absorption spectra of a $CH_2Cl_2$ solution ($3.4 \times 10^{-5}$ M) of the ring-closed isomer 37 and a 1:1 mixture of 33 and diethyl dicyanofumarate obtained after the irradiation of 37 with light of wavelengths greater than 434 nm. (c) The UV-VIS absorption spectrum of a 1:1 mixture (in $CH_2Cl_2$) of the ring-closed compounds 36 and 37 before (dark grey) and after irradiation with 430-nm light (light grey) to selectively ring-open 37. (d) The UV-VIS absorption spectrum of a 1:1 mixture (in $CH_2Cl_2$) of the ring-closed compounds 36 and 37 before (dark grey) and after irradiation with 557-nm light (light grey) to selectively ring-open 36. (e) The UV-VIS absorption spectrum of a 1:1 mixture (in $CH_2Cl_2$) of the ring-closed compounds 36 and 37 before (dark grey) and after irradiation with light greater than 434 nm (light grey) to ring open both compound.

FIG. 7 are UV-VIS absorption spectra: (a) UV-VIS absorption spectra of a CH$_2$Cl$_2$ solution (3.4×10$^{-5}$ M) of the ring-closed isomer 36 and a 1:1 mixture of 32 and diethyl dicyanofumarate obtained after the irradiation of 36 with light of wavelengths greater than 490 nm. (b) UV-VIS absorption spectra of a CH$_2$Cl$_2$ solution (3.4×10$^{-5}$ M) of the ring-closed isomer 37 and a 1:1 mixture of 33 and diethyl dicyanofumarate obtained after the irradiation of 37 with light of wavelengths greater than 434 nm. (c) The UV-VIS absorption spectrum of a 1:1 mixture (in CH$_2$Cl$_2$) of the ring-closed compounds 36 and 37 before (dark grey) and after irradiation with 430-nm light (light grey) to selectively ring-open 37. (d) The UV-VIS absorption spectrum of a 1:1 mixture (in CH$_2$Cl$_2$) of the ring-closed compounds 36 and 37 before (dark grey) and after irradiation with 557-nm light (light grey) to selectively ring-open 36. (e) The UV-VIS absorption spectrum of a 1:1 mixture (in CH$_2$Cl$_2$) of the ring-closed compounds 36 and 37 before (dark grey) and after irradiation with light greater than 434 nm (light grey) to ring open both compound. These data confirm that the release compounds can be selectively released from the thermally stable compounds 36 and 37.

Figure 8:
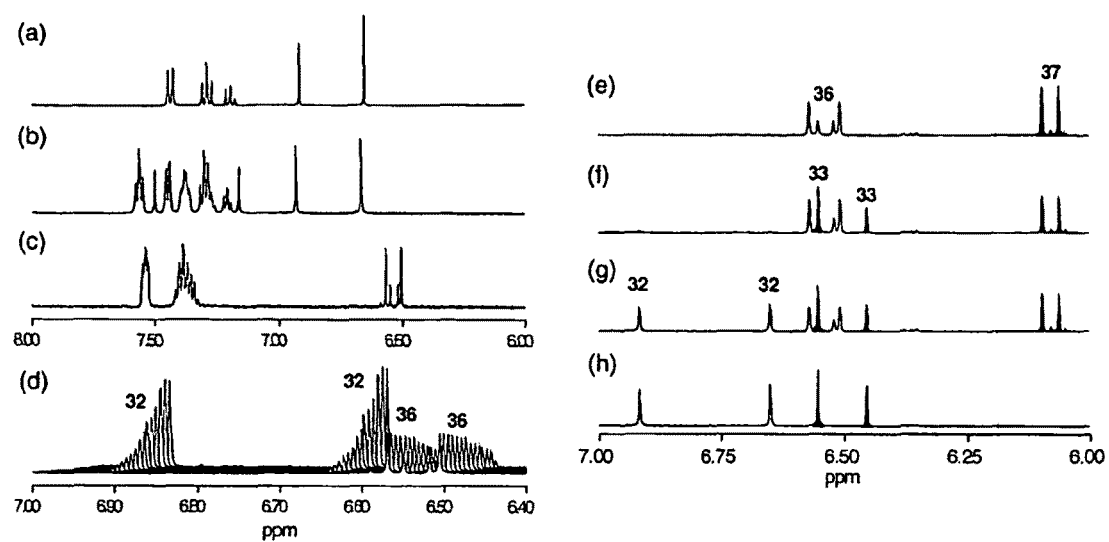
FIG. 8 are partial $^1$H NMR (500 MHz, CD$_2$Cl$_2$) spectra showing the peaks corresponding to the aromatic protons in (a) fulvene 32, (b) a 1:1 mixture of 32 and diethyl dicyanofumarate measured when the equilibrium with 34 has been reached, (c) the isolated mixture of ring-closed stereoisomers 36 and (d) a solution of 36 that has been periodically irradiated with greater than 490 nm light showing the disappearance of the ring-closed compounds 36 and the appearance of fulvene 32. The partial $^1$H NMR spectra of (e) a 1:1 mixture of 36 and 37 before irradiation (f) after irradiating with 430-nm light to partially ring-open compound 37, (g) after irradiating the same sample with greater than 557-nm light to partially ring-open compound 36 and (h) after irradiating the same sample with greater than 434-nm light to fully ring-open both compounds.

FIG. 8 are partial $^1$H NMR (500 MHz, CD$_2$Cl$_2$) spectra showing the peaks corresponding to the aromatic protons in (a) fulvene 32, (b) a 1:1 mixture of 32 and diethyl dicyanofumarate measured when the equilibrium with 34 has been reached, (c) the isolated mixture of ring-closed stereoisomers 36 and (d) a solution of 36 that has been periodically irradiated with greater than 490 nm light showing the disappearance of the ring-closed compounds 36 and the appearance of fulvene 32. The partial $^1$H NMR spectra of (e) a 1:1 mixture of 36 and 37 before irradiation (1) after irradiating with 430-nm light to partially ring-open compound 37, (g) after irradiating the same sample with greater than 557-nm light to partially ring-open compound 36 and (h) after irradiating the same sample with greater than 434-nm light to fully ring-open both compounds. These data confirm that the release compounds can be selectively released from the thermally stable compounds 36 and 37.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications and publications referred to herein are incorporated by reference in their entirety.

What is claimed is:

1. A precursor for preparation of a photoactive hexatriene compound, wherein the precursor is represented by formula II:

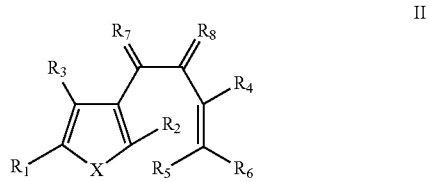

wherein,
X is S, N or O;
R$_1$ is selected from the group consisting of H, a halogen, methyl and aryl;
R$_2$ is selected from the group consisting of methyl and aryl;
R$_3$ is selected from the group consisting of H and methyl;
R$_4$ is selected from the group consisting of H, methyl, aryl, an electron-donating group, an electron-accepting group, n-C$_3$H$_7$, C$_5$H$_4$, 4-C$_6$H$_4$OCH$_3$, 3,4,5-C$_6$H$_2$(OCH$_3$)$_3$, 4-C$_6$H$_4$-NO$_2$ and 4-pyridyl, and a constituent of an optionally substituted heterocycle;
R$_5$ is selected from the group consisting of methyl, aryl, an electron-donating group and an electron-accepting group;
R$_6$ is selected from the group consisting of methyl, aryl, an electron-donating group, an electron-accepting group, and a constituent of an optionally substituted heterocycle; and
R$_7$ and R$_8$ are each carbon-containing groups, or when taken together form a 5-membered ring substituted by H or a halogen, or together form an optionally substituted 6-membered ring;
wherein the electron-donating group is selected from the group consisting of phenols, phenol ethers, anilines, thiophenes, and sulfides, and wherein the electron-accepting group is selected from the group consisting of carbonyl-based functional groups, nitriles, nitrobenzene, and pyridine.

2. The precursor of claim 1, wherein the precursor is photochemically inert.

3. The precursor of claim 1, wherein the R$_7$ and R$_8$ are each CH$_2$.

4. The precursor of claim 1 wherein the $R_7$ and $R_8$ taken together form a 6-membered ring according to

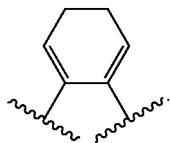 [SMILES: *C1=CCCC=C1*]

5. The precursor of claim 1, wherein the $R_7$ and $R_8$ when taken together form a cyclopentadiene, or an optionally substituted cyclopentadiene.

6. The precursor of claim 5, wherein the optionally substituted cyclopentadiene is a fulvene.

7. The precursor of claim 6 wherein the fulvene is

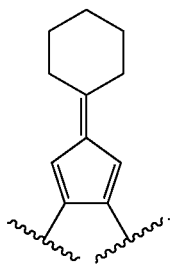 [SMILES: *C1=CC(=C2CCCCC2)C=C1*]

8. The precursor of claim 1, wherein $R_7$ and $R_8$ together form a 5-membered ring substituted by H or a halogen.

9. The precursor of claim 8, wherein the halogen is fluorine.

10. The precursor of claim 1, wherein $R_4$ and $R_6$ are constituents of an optionally substituted heterocycle.

11. The precursor of claim 10, wherein the optionally substituted heterocycle is an optionally substituted thiophene.

12. The precursor of claim 11 wherein the optionally substituted thiophene is

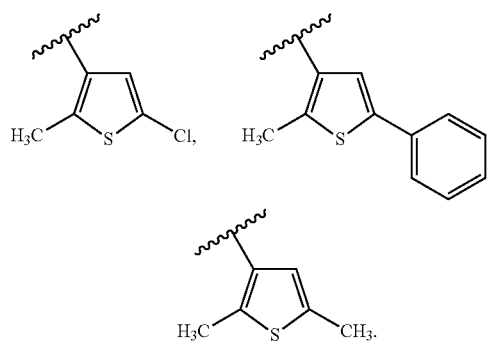

13. The precursor of claim 3, wherein:
$R_1$ is methyl;
$R_2$ is methyl;
$R_3$ is H; and
$R_5$ is methyl.

14. The precursor of claim 3, wherein:
$R_1$ is aryl;
$R_2$ is methyl;
$R_3$ is H; and
$R_5$ is methyl.

15. The precursor of claim 3, wherein:
$R_1$ is halogen;
$R_2$ is methyl;
$R_3$ is H; and
$R_5$ is methyl.

16. The precursor of claim 1 wherein the halogen is F.

17. The precursor of claim 1 wherein when $R_4$ is an electron donating group, $R_5$ and $R_6$ are electron accepting groups.

18. The precursor of claim 1 wherein when $R_4$ is an electron accepting group, $R_5$ and $R_6$ are electron donating groups.

19. The precursor of claim 1 wherein X is S.

20. The precursor of claim 1 wherein $R_4$ is selected from the group consisting of n-$C_3H_7$, $C_5H_4$, 4-$C_6H_4OCH_3$, 3,4,5-$C_6H_2(OCH_3)_3$, 4-$C_6H_4$—$NO_2$ and 4-pyridyl.

21. The precursor of claim 1, wherein the precursor is:

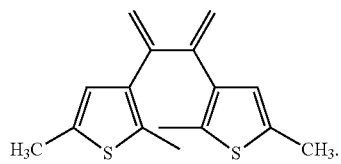

22. The precursor of claim 1, wherein the precursor is:

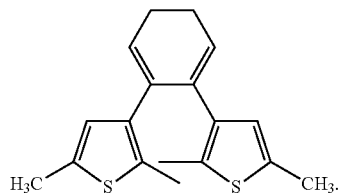

23. The precursor of claim 1, wherein the precursor is:

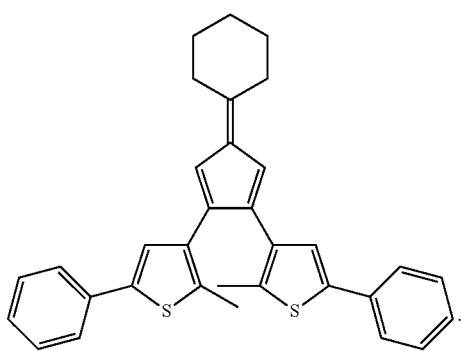

24. The precursor of claim 1, wherein the precursor is:

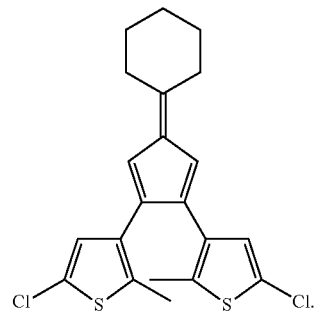

25. A method of selectively releasing a releasable agent, comprising:
  a) providing a precursor compound represented by formula II:

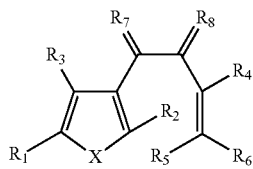

wherein,
  X is S, N or O;
  $R_1$ is selected from the group consisting of H, a halogen, methyl and aryl;
  $R_2$ is selected from the group consisting of methyl and aryl;
  $R_3$ is selected from the group consisting of H and methyl;
  $R_4$ is selected from the group consisting of H, methyl, aryl, an electron-donating group, an electron-accepting group, n-$C_3H_7$, $C_5H_4$, 4-$C_6H_4OCH_3$, 3,4,5-$C_6H_2$($OCH_3$)$_3$, 4-$C_6H_4$—$NO_2$ and 4-pyridyl, and a constituent of an optionally substituted heterocycle;
  $R_5$ is selected from the group consisting of methyl, aryl, an electron-donating group and an electron-accepting group;
  $R_6$ is selected from the group consisting of methyl, aryl, an electron-donating group, an electron-accepting group, and a constituent of an optionally substituted heterocycle; and
  $R_7$ and $R_8$ are each carbon-containing groups, or when taken together form a 5-membered ring substituted by H or a halogen, or together form an optionally substituted 6-membered ring;
  wherein the electron-donating group is selected from the group consisting of phenols, phenol ethers, anilines, thiophenes, and sulfides, and wherein the electron-accepting group is selected from the group consisting of carbonyl-based functional groups, nitriles, nitrobenzene, and pyridine;
  b) reacting the precursor compound with the releasable agent to form a carrier compound, wherein the carrier compound comprises a switching moiety reversibly convertible between a first thermally unstable form and a second thermally stable form in response to a light or an electrical stimulus; and
  c) selectively converting the switching moiety between the second form and the first form to cause controlled release of the releasable agent from the carrier compound.

26. The method of claim 25, wherein the releasable agent is a small molecule.

27. The method of claim 25, wherein the step of selectively converting the switching moiety comprises exposing the carrier compound to a predetermined wavelength of light.

28. The method of claim 25, wherein the carrier compound is delivered to a target location prior to the step of selectively converting the switching moiety.

29. The method of claim 28, wherein the target location is located in vivo.

30. The method of claim 25, wherein the precursor is photochemically inert.

31. The method of claim 26, wherein the small molecule is selected from the group consisting of therapeutic agents, biochemical effectors, polymer precursors and chemical reagents.

32. The method of claim 25, further comprising:
  a) providing multiple releasable agents;
  b) coupling each of the multiple releasable agents to the carrier compound; and
  c) selectively releasing the multiple releasable agents by sequentially exposing the carrier compound to different wavelength of light, each of the wavelengths corresponding to at least one of the releasable agents.

33. A method of synthesizing a photoactive hexatriene compound, the method comprising:
  a) providing a photochemically inert precursor compound represented by formula II:

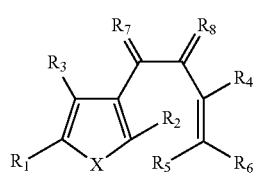

wherein,
  X is S, N or O;
  $R_1$ is selected from the group consisting of H, a halogen, methyl and aryl;
  $R_2$ is selected from the group consisting of methyl and aryl;
  $R_3$ is selected from the group consisting of H and methyl;
  $R_4$ is selected from the group consisting of H, methyl, aryl, an electron-donating group, an electron-accepting group, n-$C_3H_7$, $C_5H_4$, 4-$C_6H_4OCH_3$, 3,4,5-$C_6H_2$($OCH_3$)$_3$, 4-$C_6H_4$—$NO_2$ and 4-pyridyl, and a constituent of an optionally substituted heterocycle;
  $R_5$ is selected from the group consisting of methyl, aryl, an electron-donating group and an electron-accepting group;
  $R_6$ is selected from the group consisting of methyl, aryl, an electron-donating group, an electron-accepting group, and a constituent of an optionally substituted heterocycle; and
  $R_7$ and $R_8$ are each carbon-containing groups, or when taken together form a 5-membered ring substituted by H or a halogen, or together form an optionally substituted 6-membered ring;
  wherein the electron-donating group is selected from the group consisting of phenols, phenol ethers, anilines, thiophenes, and sulfides, and wherein the electron-accepting group is selected from the group consisting of carbonyl-based functional groups, nitriles, nitrobenzene, and pyridine; and
  h) chemically reacting the precursor compound with a reactant to form the photoactive hexatriene compound.

34. The method of claim 33, wherein the step of chemically reacting the precursor and the reactant is reversible.

35. The method of claim 33, wherein the chemically reacting is a condensation reaction.

36. The method of claim 33, wherein the chemically reacting is a cycloaddition.

* * * * *